US012714314B2

(12) United States Patent
Lee et al.

(10) Patent No.: US 12,714,314 B2
(45) Date of Patent: Aug. 25, 2026

(54) BODY TEMPERATURE ESTIMATION SYSTEM AND METHOD CONSIDERING MOVEMENTS OF TARGET PERSON AND CHANGES IN EXTERNAL TEMPERATURE

(71) Applicants: KOREA ELECTRONICS TECHNOLOGY INSTITUTE, Seongnam-si (KR); Namsung InfraNet Co., Ltd., Seoul (KR)

(72) Inventors: Min Goo Lee, Seoul (KR); Yong Kuk Park, Seoul (KR)

(73) Assignees: KOREA ELECTRONICS TECHNOLOGY INSTITUTE, Seongnam-si (KR); NAMSUNG INFRANET CO., LTD., Seoul (KR)

( * ) Notice: Subject to any disclaimer, the term of this patent is extended or adjusted under 35 U.S.C. 154(b) by 774 days.

(21) Appl. No.: 18/053,906

(22) Filed: Nov. 9, 2022

(65) Prior Publication Data

US 2024/0148255 A1 May 9, 2024

(51) Int. Cl.
*A61B 5/01* (2006.01)
*A61B 5/00* (2006.01)
(Continued)

(52) U.S. Cl.
CPC .............. *A61B 5/01* (2013.01); *A61B 5/1114* (2013.01); *A61B 5/1123* (2013.01);
(Continued)

(58) Field of Classification Search
CPC ....... A61B 5/01; A61B 5/1114; A61B 5/1123; A61B 5/6833; A61B 5/721; A61B 5/7246;
(Continued)

(56) References Cited

U.S. PATENT DOCUMENTS 11,517,203 B2 * 12/2022 Reifman ................ G16H 50/30
2018/0092545 A1 * 4/2018 Kim ..................... A61B 5/7275
(Continued)

FOREIGN PATENT DOCUMENTS

KR 10-1855573 B1 5/2018
KR 10-2021-0121359 A 10/2021
KR 20210121360 A * 10/2021 ........... A61B 5/0008

OTHER PUBLICATIONS

Office Action issued on Aug. 22, 2025, for corresponding Singapore Patent Application No. 10202251411X (5 pages).
(Continued)

*Primary Examiner* — Devin B Henson
*Assistant Examiner* — Molly Halprin
(74) *Attorney, Agent, or Firm* — Hauptman Ham, LLP

(57) ABSTRACT

A system and method are proposed for estimating the body temperature of a target person in consideration of movements of the target person and changes in the external temperature due to a sudden change in the space temperature when continuously measuring the body temperature. The body temperature estimation system includes a temperature measurement unit, a movement measurement unit, and a body temperature estimation unit. The temperature measurement unit is attached to a skin of the target person and measures a skin temperature and an external temperature. The movement measurement unit measures movements of the target person. The body temperature estimation unit estimates the body temperature based on a correlation between the skin temperature and the external temperature, and monitors a change in the external temperature per monitoring time.

7 Claims, 13 Drawing Sheets

(51) Int. Cl.
*A61B 5/11* (2006.01)
*G01K 13/20* (2021.01)

(52) U.S. Cl.
CPC ............ *A61B 5/6833* (2013.01); *A61B 5/721* (2013.01); *A61B 5/7246* (2013.01); *A61B 5/7264* (2013.01); *G01K 13/20* (2021.01); *A61B 2560/0252* (2013.01); *A61B 2562/0219* (2013.01); *A61B 2562/0271* (2013.01); *A61B 2562/164* (2013.01)

(58) Field of Classification Search
CPC .......... A61B 5/7264; A61B 2560/0252; A61B 2562/0219; A61B 2562/0271; A61B 2562/164; G01K 13/20; G01K 1/024; G01K 3/10; G01K 7/427
USPC .......................................................... 600/549
See application file for complete search history.

(56) References Cited

U.S. PATENT DOCUMENTS

| | | | |
|---|---|---|---|
| 2018/0184908 A1 | 7/2018 | Meyerson et al. | |
| 2021/0096032 A1* | 4/2021 | Lane .................... | G01K 13/223 |
| 2021/0106238 A1 | 4/2021 | Strasser et al. | |
| 2021/0204819 A1 | 7/2021 | Kim et al. | |
| 2022/0358372 A1 | 11/2022 | Nishikawa et al. | |

OTHER PUBLICATIONS

Office Action issued on Jul. 24, 2025, for U.S. Appl. No. 18/053,902 (16 pages).

* cited by examiner

Figure 10:
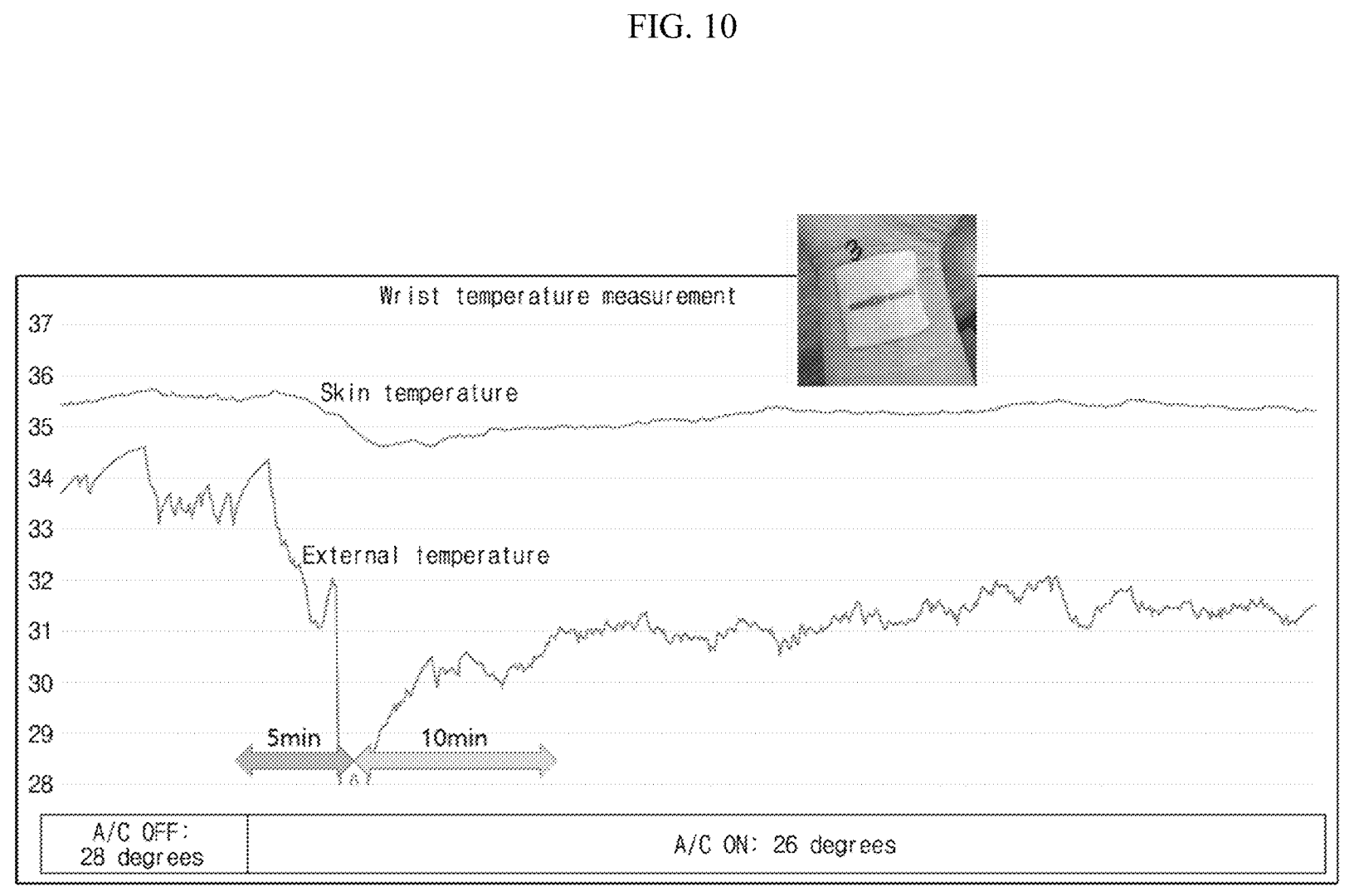

Wrist temperature measurement
Skin temperature
External temperature
5min
10min
A/C OFF: 28 degrees
A/C ON: 26 degrees
37
36
35
34
33
32
31
30
29
28

| | 15:30 | 16:09 | 16:25 | 16:30 | 16:33 | 16:36 | 16:40 | 16:43 | 16:46 | 16:50 | 16:53 | 16:57 | 17:00 | 17:03 | 17:06 | 17:09 | 17:12 | 17:15 |
|---|---|---|---|---|---|---|---|---|---|---|---|---|---|---|---|---|---|---|
| series1 | 36.6 | 36.5 | 36.6 | 36.5 | 36.5 | 36.6 | 36.5 | 36.6 | 36.6 | 36.6 | 36.6 | 36.6 | 36.6 | 36.6 | 36.5 | 36.5 | 36.6 | 36.6 |

Measured body temperature
Skin temperature
External temperature
$t_1$
$t_2$

FIG. 14

| Sample #3 (Wrist) | | Out | In | Out | In |
|---|---|---|---|---|---|
| 4254 | 16:24:30 | 34.05 | 35.6 | 0 | 0 |
| 4255 | 16:24:35 | 34.1 | 35.6 | | |
| 4256 | 16:24:40 | 34.14 | 35.59 | | |
| 4257 | 16:24:45 | 34.17 | 35.61 | | |
| 4258 | 16:24:50 | 34.21 | 36.6 | | |
| 4259 | 16:24:55 | 34.25 | 35.62 | | |
| 4260 | 16:25:00 | 34.28 | [illegible] | | |
| 4261 | 16:25:05 | 34.3 | [illegible] | | |
| 4262 | 16:25:10 | 34.33 | 35.62 | | |
| 4263 | 16:25:15 | 34.35 | 35.64 | | |
| 4264 | 16:25:20 | 33.86 | 35.65 | | |
| 4265 | 16:25:25 | 33.62 | 35.7 | | |
| 4266 | 16:25:30 | 33.38 | 35.7 | 0.67 | -0.1 |
| 4267 | 16:25:35 | 33.12 | 35.7 | | |
| 4268 | 16:25:40 | 33 | 35.68 | | |
| 4269 | 16:25:45 | 33.03 | 35.66 | | |
| 4270 | 16:25:50 | 32.68 | 35.65 | | |
| 4271 | 16:25:55 | 32.69 | 35.65 | | |
| 4272 | 16:26:00 | 32.78 | 35.66 | | |
| 4273 | 16:26:05 | 32.67 | 35.62 | | |
| 4274 | 16:26:10 | 35.57 | 35.63 | | |
| 4275 | 16:26:15 | 32.44 | 35.62 | | |
| 4276 | 16:26:20 | 32.33 | 35.61 | | |
| 4277 | 16:26:25 | 32.42 | 35.61 | | |
| 4278 | 16:26:30 | 32.24 | 35.61 | 1.34 | 0.09 |
| 4279 | 16:26:35 | 32.27 | 35.58 | | |
| 4280 | 16:26:40 | 32.32 | 35.58 | | |
| 4281 | 16:26:45 | 32.22 | 35.57 | | |
| 4282 | 16:26:50 | 32.1 | 35.57 | | |
| 4283 | 16:26:55 | 31.94 | 35.55 | | |
| 4284 | 16:27:00 | 31.89 | 35.55 | | |
| 4285 | 16:27:05 | 31.54 | 35.55 | | |
| 4286 | 16:27:10 | 31.33 | 35.51 | | |
| 4287 | 16:27:15 | 31.18 | 35.49 | | |
| 4288 | 16:27:20 | 31.16 | 35.46 | | |
| 4289 | 16:27:25 | 31.21 | 35.45 | | |
| 4290 | 16:27:30 | 31.17 | 35.42 | 1.07 | 0.19 |
| 4291 | 16:27:35 | 31.06 | 35.41 | | |
| 4292 | 16:27:40 | 31.08 | 35.38 | | |
| 4293 | 16:27:45 | 31.1 | 35.36 | | |
| 4294 | 16:27:50 | 31.21 | 35.33 | | |
| 4295 | 16:27:55 | 31.42 | 35.29 | | |
| 4296 | 16:28:00 | 31.61 | 35.26 | | |
| 4297 | 16:28:05 | 31.76 | 35.28 | | |
| 4298 | 16:28:10 | 31.89 | 35.27 | | |
| 4299 | 16:28:15 | 32.03 | 35.25 | | |
| 4300 | 16:28:20 | 31.92 | 35.27 | | |
| 4301 | 16:28:25 | 31.87 | 35.24 | | |
| 4302 | 16:28:30 | 29.35 | 35.25 | 1.82 | 0.17 |
| 4303 | 16:28:35 | 28.28 | 35.22 | | |
| 4304 | 16:28:40 | 27.42 | 35.19 | | |
| 4305 | 16:28:45 | 27.3 | 35.15 | | |
| 4306 | 16:28:50 | 27.14 | 35.13 | | |
| 4307 | 16:28:55 | 27.07 | 35.05 | | |

BODY TEMPERATURE ESTIMATION SYSTEM AND METHOD CONSIDERING MOVEMENTS OF TARGET PERSON AND CHANGES IN EXTERNAL TEMPERATURE

CROSS-REFERENCE TO RELATED APPLICATION

The present application relates to a concurrently-filed U.S. patent application Ser. No. 18/053,902, entitled "BODY TEMPERATURE ESTIMATION SYSTEM AND METHOD BASED ON ONE-CHANNEL TEMPERATURE SENSOR," which is incorporated herein in its entirety by reference.

TECHNICAL FIELD

The present disclosure relates to a body temperature estimation technology, and more particularly, to a system and method for estimating the body temperature of a target person in consideration of movements of the target person and changes in the external temperature due to a sudden change in the space temperature when continuously measuring the body temperature.

BACKGROUND

Recently, in the medical industry, efforts to create new types of medical devices or medical services by convergence of information and communications technologies (ICT) are expanding. For example, research is being conducted to collect and analyze patient's bio-signals in real time by attaching sensors of various uses and types to the patient and utilize the patient's biometric information for treatment of the patient.

In the biometric information, body temperature is the most basic diagnostic information and is an index that reflects various physiological changes. Temperature measurement is mandatory for most diseases. Recently, the importance of measuring the body temperature has been further emphasized due to the influence of COVID-19.

SUMMARY

The present disclosure provides a system and method for estimating the body temperature of a target person in consideration of movements of the target person and changes in the external temperature due to a sudden change in the space temperature when continuously measuring the body temperature.

According to the present disclosure, a wearable temperature patch attached to a target person's skin and continuously estimating a body temperature may include a flexible base film including a first base film and a second base film connected to the first base film and bent over the first base film; a skin temperature sensor mounted on a lower surface of the first base film, being in contact with the target person's skin, and measuring a skin temperature at regular intervals; an external temperature sensor mounted on an upper surface of the second base film and measuring an external temperature outside the target person's skin at the regular intervals; an inertia measurer installed on the first base film and measuring movements of the target person; a controller installed on the first base film, receiving measured movement information from the inertial measurer, receiving the measured skin temperature from the skin temperature sensor, receiving the measured external temperature from the external temperature sensor, estimating the body temperature based on a correlation between the skin temperature and the external temperature, monitoring a change in the external temperature per monitoring time, if the change in the external temperature is greater than or equal to a threshold, estimating a body temperature before the change in the external temperature greater than or equal to the threshold occurs as a current body temperature, and correcting the estimated current body temperature by reflecting the received movement information; and a ground layer formed on the first base film to be spaced apart from a mounting region in which the skin temperature sensor is mounted.

The first base film may have a heat conduction blocking slot formed for blocking heat conduction to the mounting region. In addition, the heat conduction blocking slot may include a guard slot formed in the first base film along circumference of the skin temperature sensor, and a boundary slot formed at a boundary between the mounting region and a region in which the ground layer is formed.

In the wearable temperature patch, the controller may classify the received movement information according to a movement type and a movement intensity, and estimate the current body temperature by reflecting a weight corresponding to the classified movement information.

In the wearable temperature patch, the monitoring time may be 1 to 5 minutes.

In the wearable temperature patch, the threshold may be 0.5 or higher.

In the wearable temperature patch, the controller may calculate the amount of change in the external temperature by Equation 1 below, if the change amount of the external temperature calculated in the monitoring time of $(t_{i+1}-t_i)$ is greater than or equal to the threshold, replace the external temperature and skin temperature measured at time $t_{i+1}$ with the external temperature and skin temperature measured at time $t_i$, and estimate the body temperature at time $t_{i+1}$ based on the correlation between the replaced skin temperature and external temperature.

$$\Delta T = T_i - T_{i+1} \quad \text{[Equation 1]}$$

$T_i$: External temperature at time $t_i$ $T_{i+1}$: External temperature at time $t_{i+1}$ $t_{i+1}-t_i$: Monitoring time In the wearable temperature patch, the correlation may be expressed by Equation 2 below.

$$T_{est}(t) = (k*T_2(t-\alpha)-T_3(t))/(k-1) \quad \text{[Equation 2]}$$

$T_{est}$: Estimated body temperature k: External influence proportional constant $T_2$: External temperature $T_3$: Skin temperature t: Measurement time (unit: minutes)

$\alpha$: Temperature transfer time (unit: minutes)

According to the present disclosure, a body temperature estimation system continuously estimating a body temperature of a target person may include a temperature measurement unit attached to a skin of the target person and measuring a skin temperature and an external temperature; a movement measurement unit measuring movements of the target person; and a body temperature estimation unit receiving measured movement information from the movement measurement unit, receiving the skin temperature and the external temperature from the temperature measurement unit, estimating the body temperature based on a correlation between the skin temperature and the external temperature, monitoring a change in the external temperature per monitoring time, if the change in the external temperature is greater than or equal to a threshold, estimating a body temperature before the change in the external temperature greater than or equal to the threshold occurs as a current body temperature, and correcting the estimated current body temperature by reflecting the received movement information.

In addition, the temperature measurement unit may include a flexible base film including a first base film and a second base film connected to the first base film and bent over the first base film; a skin temperature sensor mounted on a lower surface of the first base film, being in contact with the skin, and measuring the skin temperature; an external temperature sensor mounted on an upper surface of the second base film and measuring the external temperature; and a ground layer formed on the first base film to be spaced apart from a mounting region in which the skin temperature sensor is mounted/

The first base film may have a heat conduction blocking slot formed for blocking heat conduction to the mounting region, and the heat conduction blocking slot may include a guard slot formed in the first base film along circumference of the skin temperature sensor, and a boundary slot formed at a boundary between the mounting region and a region in which the ground layer is formed.

According to the present disclosure, a body temperature estimation system continuously estimating a body temperature of a target person may include a wearable temperature patch attached to a skin of the target person and continuously estimating the body temperature; and a management terminal receiving the estimated body temperature of the target person from the wearable temperature patch.

The wearable temperature patch may include a flexible base film including a first base film and a second base film connected to the first base film and bent over the first base film; a skin temperature sensor mounted on a lower surface of the first base film, being in contact with the target person's skin, and measuring a skin temperature; an external temperature sensor mounted on an upper surface of the second base film and measuring an external temperature outside the target person's skin; an inertia measurer installed on the first base film and measuring movements of the target person; a controller installed on the first base film, receiving measured movement information from the inertial measurer, receiving the measured skin temperature from the skin temperature sensor, receiving the measured external temperature from the external temperature sensor, estimating the body temperature based on a correlation between the skin temperature and the external temperature, monitoring a change in the external temperature per monitoring time, if the change in the external temperature is greater than or equal to a threshold, estimating a body temperature before the change in the external temperature greater than or equal to the threshold occurs as a current body temperature, and correcting the estimated current body temperature by reflecting the received movement information; and a ground layer formed on the first base film to be spaced apart from a mounting region in which the skin temperature sensor is mounted.

The first base film may have a heat conduction blocking slot formed for blocking heat conduction to the mounting region, and the heat conduction blocking slot may include a guard slot formed in the first base film along circumference of the skin temperature sensor, and a boundary slot formed at a boundary between the mounting region and a region in which the ground layer is formed.

According to the present disclosure, even if a sudden change in the temperature of a space in which a target person is located occurs, the body temperature of the target person can be more accurately estimated in consideration of the movement of the target person and the sudden change in the external temperature together.

When the amount of change in the external temperature measured per monitoring time is greater than or equal to a threshold, the wearable temperature patch attached to the target person's skin estimates, as the current body temperature, a body temperature estimated before the change in the external temperature occurs. That is, a change in the external temperature caused by the external environment occurring in a short time may cause a large error between the actual body temperature of the target person and the body temperature estimated by the wearable temperature patch. Therefore, in the present disclosure, in the case that a sudden change in the external temperature occurs in a short time, the current external temperature is ignored when estimating the body temperature by reflecting the skin temperature and external temperature measured by the wearable temperature patch, and the body temperature of the target person is estimated by reflecting the external temperature and skin temperature before the temperature change occurs. That is, the wearable temperature patch estimates, as the current body temperature at the time the temperature change occurs, the body temperature estimated by reflecting the external temperature and skin temperature before the sudden external temperature change occurs. This allows correcting the error of the estimated body temperature due to the sudden external temperature change.

Therefore, since it is possible to correct the body temperature measurement error due to a sudden temperature change in the external environment, it is expected that more accurate and continuous body temperature measurement will be possible and the use of wearable temperature patches attachable to the skin will be expanded.

In addition, the wearable temperature patch according to the present invention is a wearable type that can be attached to the skin of a target person and enables continuous body temperature measurement in daily life, so it is expected to be used for medical staff to determine the diagnosis of an infectious disease through a more accurate long-term continuous temperature measurement record during social chaos such as the recent COVID-19 epidemic.

Further, the body temperature estimation method using the wearable temperature patch according to the present disclosure can more accurately estimate the body temperature of the target person by reflecting movement information in an environment in which a sudden change in the external temperature occurs. That is, for a sudden external temperature change, by using the movement information measured by the wearable temperature patch, it is possible to distinctively determine whether the temperature change is caused by the movement of the target person in space or caused by the operation of an air conditioner or heater. In this case, the body temperature may be estimated based on the correlation between the external temperature and the skin temperature before the sudden external temperature change, and the body temperature of the target person may be more accurately estimated by reflecting the weight of the movement information to the estimated body temperature.

BRIEF DESCRIPTION OF THE DRAWINGS

FIG. 1 is a block diagram illustrating a body temperature estimation system in consideration of movements of a target person and changes in the external temperature according to the present disclosure.

FIG. 2 is a block diagram illustrating a body temperature estimation system in consideration of movements of a target person and changes in the external temperature according to an embodiment of the present disclosure.

FIG. 10 is a graph showing the skin temperature and the external temperature measured by the wearable temperature patch in an environment of a rapid change in the spatial temperature.

FIG. 12 is a graph showing the skin temperature, external temperature, and body temperature measured in the environment of rapid space temperature change of FIG. 10.

FIG. 13 is a graph showing normalization of the skin temperature, external temperature, and body temperature measured in a problem section of FIG. 12.

FIG. 14 is a table showing the skin temperature, the external temperature, and the amount of change in temperature measured in units of one minute in the environment of rapid space temperature change of FIG. 10.

DETAILED DESCRIPTION

Figure 3:
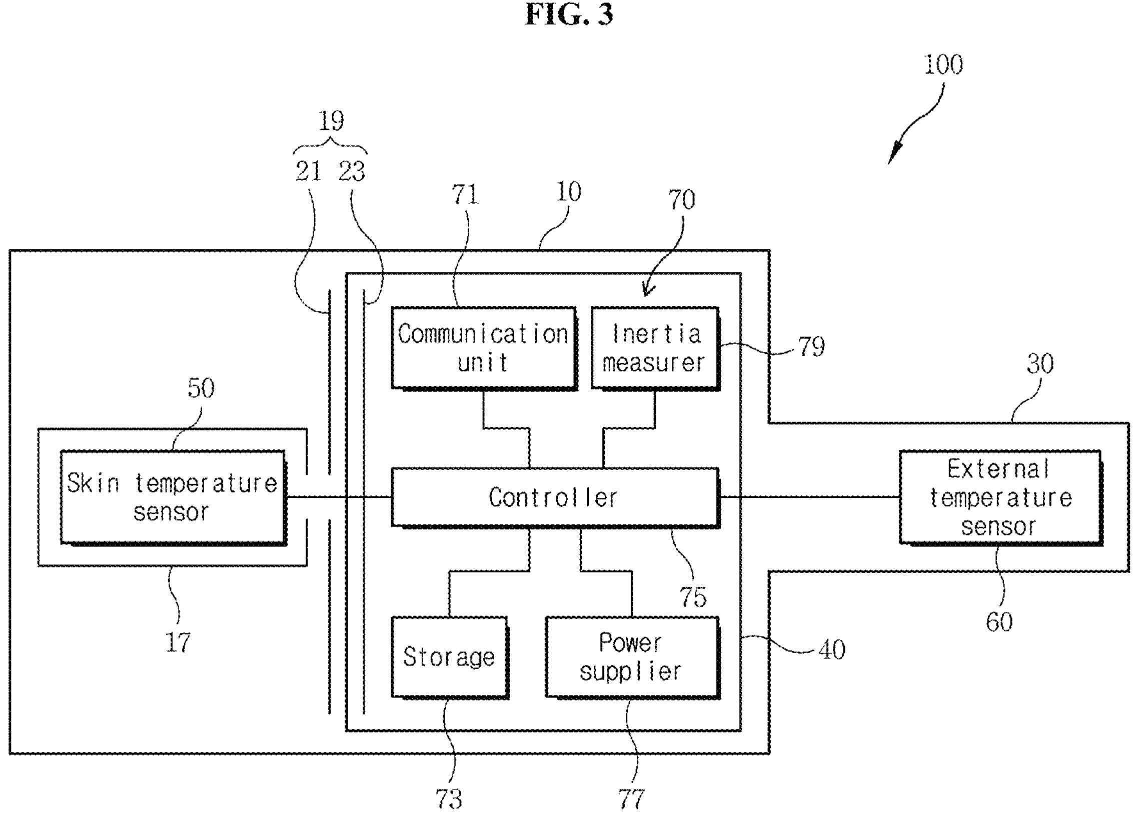
FIG. 3 is a block diagram illustrating the wearable temperature patch of FIG. 2.

In the case that a target person is a patient, the existing body temperature measurement method is a regular check method in which a nurse visits a hospital room at a certain time to measure and record the patient's body temperature. Recently, research and attempts to measure the body temperature by using a medical patch attached to human skin are being actively conducted. This method is to automatically measure and record the body temperature for a long period of time through the medical patch without the patient's reluctance, so it can minimize the discomfort of patients due to body temperature measurement and greatly reduce the work intensity of nurses caused by regular check. This is expected to enable smart and efficient medical services to be provided to patients.

However, when the body temperature is measured over a long period of time in an environment in which the target person lives with the medical patch attached to the skin, the temperature of a space in which the target person is located often affects the measured external temperature. That is, when the space temperature is rapidly changed, the external temperature also greatly changes, and thus the accuracy of body temperature estimated (measured) through the medical patch is inevitably lowered.

Now, embodiments of the present disclosure will be described in detail with reference to the accompanying drawings.

However, in the following description and the accompanying drawings, well known techniques may not be described or illustrated in detail to avoid obscuring the subject matter of the present disclosure. Through the drawings, the same or similar reference numerals denote corresponding features consistently.

The terms and words used in the following description, drawings and claims are not limited to the bibliographical meanings thereof and are merely used by the inventor to enable a clear and consistent understanding of the disclosure. Thus, it will be apparent to those skilled in the art that the following description about various embodiments of the present disclosure is provided for illustration purpose only and not for the purpose of limiting the disclosure as defined by the appended claims and their equivalents.

[Body Temperature Estimation System]

Figures 1, 2:
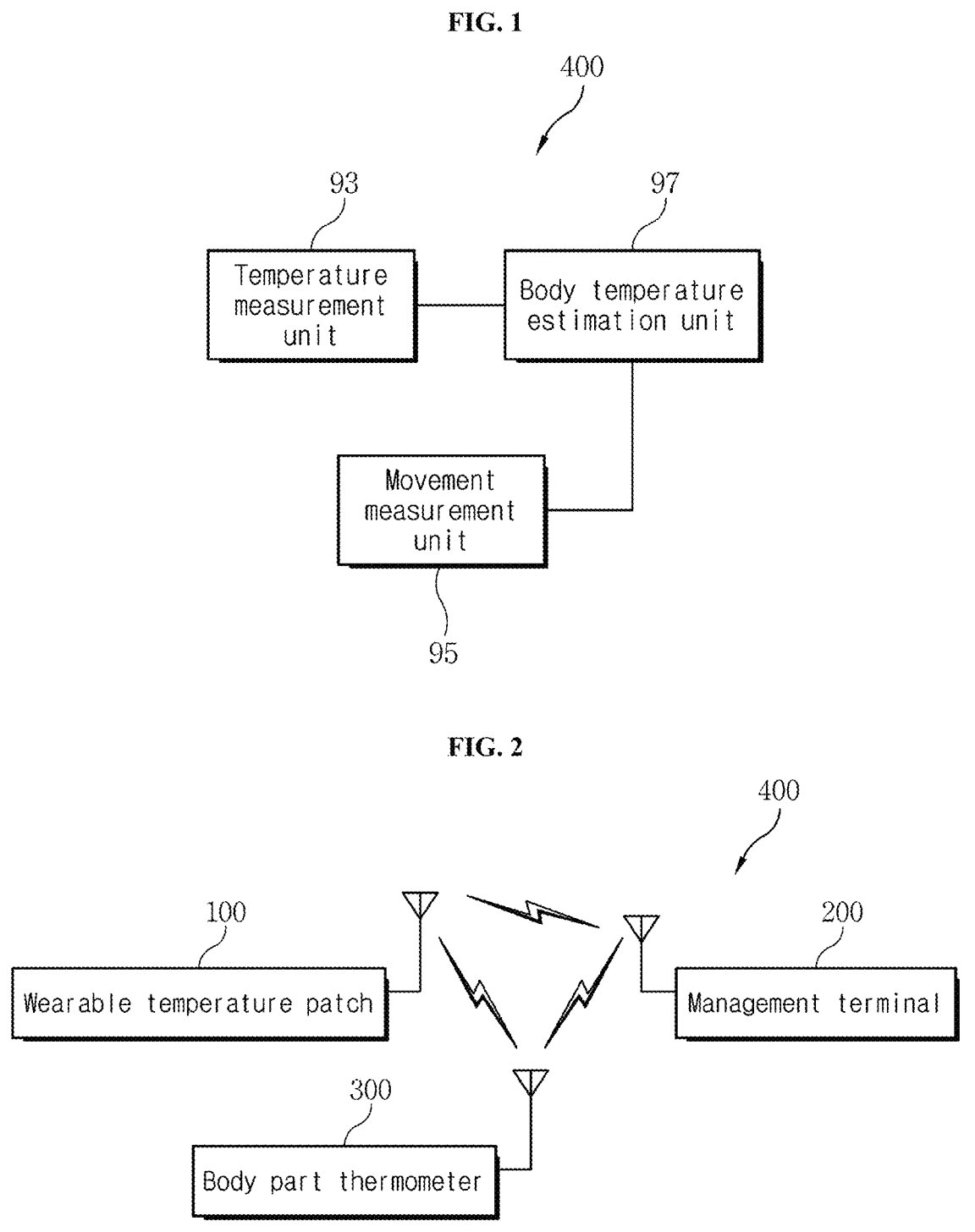

FIG. 1 is a block diagram illustrating a body temperature estimation system in consideration of movements of a target person and changes in the external temperature according to the present disclosure.

Referring to FIG. 1, a body temperature estimation system 400 in consideration of movements of a target person and changes in the external temperature according to the present disclosure (hereinafter referred to as the 'body temperature estimation system') is a system for estimating the body temperature of a target person by correcting the measured skin temperature based on the measured external temperature in providing the body temperature over a long period of time. In addition, the body temperature estimation system 400 is a system for estimating the body temperature of a target person in consideration of a sudden change in the external temperature.

The body temperature estimation system 400 includes a temperature measurement unit 93 and a body temperature estimation unit 97.

The temperature measurement unit 93 is attached to the skin of a target person and continuously measures the skin temperature and the external temperature at regular intervals.

The body temperature estimation unit 97 receives the skin temperature and the external temperature from the temperature measurement unit 93 and estimates the body temperature based on a correlation between the skin temperature and the external temperature. For example, based on a time when the skin temperature is measured, the body temperature estimation unit 97 extracts the external temperature that affects the skin temperature depending on the heat transfer characteristics of the temperature measurement unit 93. Then, from the correlation between the skin temperature and the extracted external temperature, the body temperature estimation unit 97 may estimate the body temperature of the target person at the time the skin temperature is measured.

The temperature measurement unit 93 is attached to the skin and measures the skin temperature and the external temperature at regular intervals. In this case, the regular interval may be several seconds, for example, 5 seconds. The temperature measurement unit 93 time-synchronizes the measured skin temperature and the measured external temperature and outputs them to the body temperature estimation unit 97.

The temperature measurement unit 93 may be implemented as a wearable temperature patch of a patch type that can be attached to the skin. The temperature measurement unit 93 measures the skin temperature through one surface attached to the skin, and measures the external temperature through the other surface facing the outside opposite to the skin.

The external temperature refers to a temperature (T2) acting on the skin by external heat-affecting factors (T1), such as sunlight, solar heat, outdoor temperature, heating and cooling facilities in a building, clothing, and bedding, which thermally affect the skin by the external environment. That is, the external temperature is not defined as a spatial representative temperature in terms of architecture, but is defined as a space temperature between the skin and the clothes worn by the target person. It may be considered to measure the spatial representative temperature in terms of architecture in real time and apply it to the body temperature estimation system 400, but this is not competitive in terms of cost and system configuration. Moreover, the temperature of a space between the clothes and the skin after the architectural external heat effect is filtered by the clothes is a key part influencing the estimated body temperature of the present disclosure.

The skin temperature is a body temperature detected from the skin in which the external temperature by the external heat-affecting factors is reflected.

Therefore, it is preferable that the temperature measurement unit 93 measures the external temperature at an upper point on a position where the skin temperature is measured.

The external temperature that affects the skin temperature can be extracted based on a temperature transfer time derived from Pearson's product moment correlation coefficient. The Pearson's product moment correlation coefficient is related to the heat transfer characteristics of the temperature measurement unit 93. The external temperature passes through the temperature measurement unit 93 and affects the skin temperature, and the temperature transfer time is required for the external temperature to be transmitted to the skin temperature. For example, the extracted external temperature may be an external temperature measured at a previous time (temperature transfer time) within 5 minutes based on the time at which the skin temperature is measured.

The correlation for estimating the body temperature is expressed by Equation 1 below.

$$T_{est}(t)=(k*T_2(t-\alpha)-T_3(t))/(k-1) \quad \text{[Equation 1]}$$

$T_{est}$: Estimated body temperature k: External influence proportional constant $T_2$: External temperature $T_3$: Skin temperature t: Measurement time (unit: minutes)

$\alpha$: Temperature transfer time (unit: minutes)

Here, the external influence proportional constant (k) can be calculated using a data-driven approach for external temperature and skin temperature collected from a plurality of target persons. As described above, the temperature transfer time $\alpha$ can be derived from the Pearson's product moment correlation coefficient.

The modeling of the correlation according to Equation 1 will be described later.

The body temperature estimation unit 97 estimates the body temperature of the target person, based on the skin temperature and the external temperature received from the temperature measurement unit 93. The body temperature estimation unit 97 estimates the body temperature in consideration of thermal effects in a section where a sudden temperature change occurs in a space where the target person is located. That is, the body temperature estimation unit 97 monitors the amount of change in the external temperature per monitoring time. If the change amount of the external temperature is greater than or equal to a threshold as the result of monitoring, the body temperature estimation unit 97 estimates, as the current body temperature, the body temperature estimated before the external temperature change greater than or equal to the threshold occurs. That is, when the target person is exposed to an environment in which a sudden temperature change occurs and when the external temperature change greater than or equal to the threshold occurs, the body temperature estimation unit 97 estimates the current body temperature using the body temperature estimated before the sudden temperature change as a reference value.

The monitoring time and the threshold are reference values for determining a sudden change in the external temperature. The monitoring time is 5 minutes or less and may be preferably determined between 1 minute and 5 minutes. The threshold may be determined at 0.5 or higher.

The body temperature estimation unit 97 calculates the amount of change in the external temperature in the monitoring time of $(t_{i+1}-t_i)$ by Equation 2 below. If the change amount of the external temperature calculated in the monitoring time of $(t_{i+1}-t_i)$ is greater than or equal to the threshold, the body temperature estimation unit 97 replaces the external temperature and skin temperature measured at time $t_{i+1}$ with the external temperature and skin temperature measured at time $t_i$. In addition, the body temperature estimation unit 97 estimates the body temperature at time $t_{i+1}$ based on the correlation between the replaced skin temperature and external temperature. That is, if the calculated change amount of the external temperature is greater than or equal to the threshold, the body temperature estimation unit 97 estimates the body temperature estimated at time $t_i$ as the body temperature at time $t_{i+1}$.

$$\Delta T=T_i-T_{i+1} \quad \text{[Equation 2]}$$

$T_i$: External temperature at time $t_i$ $T_{i+1}$: External temperature at time $t_{i+1}$ $t_{i+1}-t_i$: Monitoring time As such, if a sudden change in the external temperature occurs during the monitoring time, the body temperature estimation unit 97 estimates the body temperature at time $t_{i+1}$ by using the body temperature estimated at time $t_i$ as a reference value.

In addition, the body temperature estimation system 400 according to the present disclosure may further include a movement measurement unit 95. The movement measurement unit 95 measures the movement of the target person. That is, the movement measurement unit 95 measures the movement that occurs while the target person naturally moves through various spaces, and provides the measured movement to the body temperature estimation unit 97.

The body temperature estimation unit 97 may estimate the current body temperature by reflecting the movement information of the target person. The movement information includes the type and intensity of movement. For example, the type of movement may include sitting, standing, walking, running, and the like. The intensity of movement may be determined by a movement type and a movement time.

The body temperature estimation unit 97 may classify and manage the estimated body temperature by reflecting the movement of the target person, or may estimate the body temperature by giving a weight upon estimating the body temperature. That is, when detecting a sudden temperature change, the body temperature estimation unit 97 utilizes the movement information received from the movement measurement unit 95 and thereby determines whether the temperature change is caused by a spatial movement of the target person or caused by the operation of an air conditioner in a certain place. Based on the determination result, the body temperature estimation unit 97 may classify and manage the estimated body temperature. Alternatively, based on the determination result, the body temperature estimation unit 97 may estimate the body temperature by giving a weight. For example, when the sudden temperature change is caused by the spatial movement of the target person, the body temperature may normally rise due to the movement of the target person, and thus the body temperature estimation unit 97 may estimate the current body temperature by adding a weight to the body temperature estimated before the external temperature change occurs. Also, when the sudden temperature change is caused by the operation of the air conditioner, the movement of the target person hardly occurs, and thus the body temperature estimation unit 97 may estimate the body temperature estimated before the external temperature change as the current body temperature.

The above-described body temperature estimation system 400 according to the present disclosure may be implemented in embodiments shown in FIGS. 2 to 7, but this is not a limitation.

FIG. 2 is a block diagram illustrating a body temperature estimation system 400 in consideration of movements of a target person and changes in the external temperature according to an embodiment of the present disclosure.

Referring to FIG. 2, the temperature estimation system 400 according to this embodiment includes a wearable temperature patch 100 and a management terminal 200. In addition, the temperature estimation system 400 according to this embodiment may further include a body part thermometer 300.

The body part thermometer 300 measures the body temperature of a target person's body part and outputs it. The body part thermometer 300 measures the body temperature of one of chest, forehead, armpit, ear, and earlobe. The body part thermometer 300 may be a commercial thermometer.

The body part thermometer 300 is used to model the correlation for body temperature estimation according to this embodiment, and to check the accuracy of the body temperature estimated from the modeled correlation with the body temperature measured by the body part thermometer 300. In order to model the correlation for body temperature estimation, it is preferable to use the body part thermometer 300 capable of accurately measuring the body temperature. In this embodiment, a forehead thermometer is exemplarily used as the body part thermometer 300, but the present disclosure is not limited thereto.

Thus, the temperature estimation system 400 according to this embodiment may not include the body part thermometer 300.

The wearable temperature patch 100 extracts the external temperature affecting the skin temperature according to the heat transfer characteristics of the wearable temperature patch 100, based on the time the skin temperature is measured. The wearable temperature patch 100 estimates the body temperature of the target person at the time the skin temperature is measured, from the correlation between the skin temperature and the extracted external temperature.

The wearable temperature patch 100 is attached to the skin of the target person and continuously measures the skin temperature and the external temperature at regular intervals. The wearable temperature patch 100 may time-synchronize the skin temperature and the external temperature and output them. The wearable temperature patch 100 may be a flexible temperature sensor module implemented as a flexible patch type. The wearable temperature patch 100 may perform the function of the above-described temperature measurement unit.

In addition, the management terminal 200 estimates the body temperature of the target person, based on the skin temperature and external temperature received from the wearable temperature patch 100. That is, the management terminal 200 receives the skin temperature and external temperature from the wearable temperature patch 100. The management terminal 200 extracts the external temperature affecting the skin temperature according to the heat transfer characteristics of the wearable temperature patch 100, based on the time the skin temperature is measured. Also, the management terminal 200 estimates the body temperature of the target person at the time the skin temperature is measured, from the correlation between the skin temperature and the extracted external temperature. The management terminal 200 is a communication terminal used by a manager, and may be, for example, a PC, a smartphone, a notebook computer, a tablet PC, a dedicated terminal, a server, or the like. The management terminal 200 may perform the function of the above-described body temperature estimation unit.

In this embodiment, the body part thermometer 300, the wearable temperature patch 100, and the management terminal 200 are capable of performing communication in a wireless communication scheme. As the wireless communication scheme, a short-range wireless communication scheme may be used. As the short-range wireless communication scheme, Bluetooth, Bluetooth Low Energy (BLE), WiFi, Zigbee, Near Field Communication (NFC), or the like may be used.

Meanwhile, in this embodiment, the management terminal 200 is described as performing the function of the body temperature estimation unit, but the disclosure is not limited thereto.

For example, the wearable temperature patch 100 may have temperature extraction functions of the temperature measurement unit and temperature estimation unit, and the management terminal 200 may have a body temperature estimation function of the body temperature estimation unit.

That is, the wearable temperature patch 100 may measure the external temperature and the skin temperature and then extract the external temperature affecting the skin temperature according to the heat transfer characteristics of the wearable temperature patch 100, based on the time at which the skin temperature is measured. Then, the wearable temperature patch 100 may transmit the skin temperature, the external temperature, and the extracted external temperature to the management terminal 200. Also, the management terminal 200 may estimate the body temperature of the target person at the time the skin temperature is measured, from the correlation between the skin temperature and the extracted external temperature.

In addition, the management terminal 200 estimates the body temperature in consideration of the thermal effect in a section in which a sudden temperature change occurs in a space where the target person is located. That is, the management terminal 200 monitors the amount of change in the external temperature per monitoring time. As a result of monitoring, if the change amount of the external temperature is greater than or equal to a threshold, the management terminal 200 estimates the current body temperature from the body temperature estimated before the external temperature change greater than or equal to the threshold occurs.

Alternatively, the wearable temperature patch 100 may include the temperature measurement unit and the temperature estimation unit. The management terminal 200 may receive the skin temperature, the external temperature, the extracted external temperature, or the estimated body temperature from the wearable temperature patch 100 and output or manage it.

That is, the wearable temperature patch 100 may measure the external temperature and the skin temperature and then extract the external temperature affecting the skin temperature according to the heat transfer characteristics of the wearable temperature patch 100, based on the time at which the skin temperature is measured. Then, the wearable temperature patch 100 may estimate the body temperature of the target person at the time the skin temperature is measured, from the correlation between the skin temperature and the extracted external temperature.

In addition, the wearable temperature patch 100 estimates the body temperature in consideration of the thermal effect in a section in which a sudden temperature change occurs in a space where the target person is located. That is, the wearable temperature patch 100 monitors the amount of change in the external temperature per monitoring time. As a result of monitoring, if the change amount of the external temperature is greater than or equal to a threshold, the wearable temperature patch 100 estimates the current body temperature from the body temperature estimated before the external temperature change greater than or equal to the threshold occurs.

Hereinafter, the wearable temperature patch 100 according to this embodiment will be described in detail with reference to FIGS. 3 to 6.

FIG. 3 is a block diagram illustrating the wearable temperature patch 100 of FIG. 2.

Referring to FIG. 3, the wearable temperature patch 100 according to this embodiment includes flexible base films 10 and 30 and a skin temperature sensor 50. The base films 10 and 30 have a mounting region 15 in which the skin temperature sensor 50 is mounted, and also have heat conduction blocking slots 17 and 19 formed for blocking heat conduction to the mounting region 15. The skin temperature sensor 50 is mounted in the mounting region 15 of the base films 10 and 30, is in contact with the skin, and measures the skin temperature. In addition, the wearable temperature patch 100 according to this embodiment may further include an external temperature sensor 60, a ground layer 40, and a heat-generating element 70.

By forming the heat conduction blocking slots 17 and 19 around the skin temperature sensor 50, the wearable temperature patch 100 according to this embodiment can block heat conduction to the skin temperature sensor 50 through the base films 10 and 30. That is, it is possible to reduce the influence of internal heat-affecting factors with the heat conduction blocking slots 17 and 19.

The internal heat-affecting factors will be described. In a printed circuit board including the base films 10 and 30, heat generated from the skin around the skin temperature sensor 50 and heat generated during the operation of the heat-generating element 70 are conducted to the skin temperature sensor 50 through the ground layer 40 or the electrode layer in the printed circuit board, thereby affecting the measured body temperature.

Therefore, in order to block such heat effects due to the internal heat-affecting factor, the heat conduction blocking slots 17 and 19 are formed in this embodiment.

The heat conduction blocking slots 17 and 19 may include at least one of a guard slot 17 formed in the base film 10 along the circumference of the skin temperature sensor 50, and a boundary slot 19 formed near a boundary between the mounting region 15 where the skin temperature sensor 50 is mounted, and a region where the ground layer 40 is formed. The boundary slot 19 includes at least one of a first boundary slot 21 formed in the base film 10 and a second boundary slot 23 formed in the ground layer 40. In this embodiment, the guard slot 17 and the boundary slot 19 are formed together, and the first and second boundary slots 21 and 23 are formed together.

The base films 10 and 30 include a first base film 10 and a second base film 30. The second base film 30 is connected to the first base film 10 and bent over the first base film 10.

The skin temperature sensor 50, the ground layer 40, and the heat-generating element 70 are formed on the first base film 10. In addition, the external temperature sensor 60 is formed on the second base film 30.

The skin temperature sensor 50 is mounted on one side of the first base film 10.

The ground layer 40 is formed on the first base film 10 spaced apart from the mounting region 15 where the skin temperature sensor 50 is mounted.

The heat-generating element 70 is formed on the first base film 10 spaced apart from the mounting region 15 on which the skin temperature sensor 50 is mounted. In this case, the heat-generating element 70 may be formed in a region where the ground layer 40 is formed.

The heat-generating element 70 refers to an element included in the wearable temperature patch 100 and capable of affecting the skin temperature sensor 50 according to an internal heat-affecting factor. The heat-generating element 70 may include a communication unit 71, a storage 73, a controller 75, a power supplier 77, and an inertia measurer 79.

The communication unit 71 performs communication with the management terminal 200. The communication unit 71 may use a short-range wireless communication scheme as a communication scheme with the management terminal 200.

The storage 73 stores the skin temperature measured by the skin temperature sensor 50 and/or the external temperature measured by the external temperature sensor 60.

The controller 75 is a microprocessor that controls the overall operation of the wearable temperature patch 100. The controller 75 transmits the temperature measured by the skin temperature sensor 50 and the external temperature sensor 60 or the temperature stored in storage 73 to the management terminal 200 through the communication unit 71.

The power supplier 77 supplies power required for operations to the skin temperature sensor 50, the communication unit 71, the storage 73, and the controller 75. The power supplier 77 is an electrical energy storage device that can be charged and discharged multiple times, and may include, for example, at least one of a secondary battery and a super capacitor. The power supplier 77 may include an energy harvesting unit that collects energy around the wearable temperature patch 100, such as a body temperature or a wireless signal, and generates electrical energy.

The inertia measurer 79 measures the movement of the target person to which the wearable temperature patch 100 is attached. The inertia measurer 79 measures the speed, direction, gravity, and acceleration of the target person. The inertial measurer 79 recognizes and measures the movement of the target person by using an accelerometer, an angular accelerometer, a geo-magnetometer, and/or an altimeter. As described above, the inertia measurer 79 measures the movement that occurs in a process that the target person naturally moves through various spaces, and outputs it to the controller 75.

Figure 4:
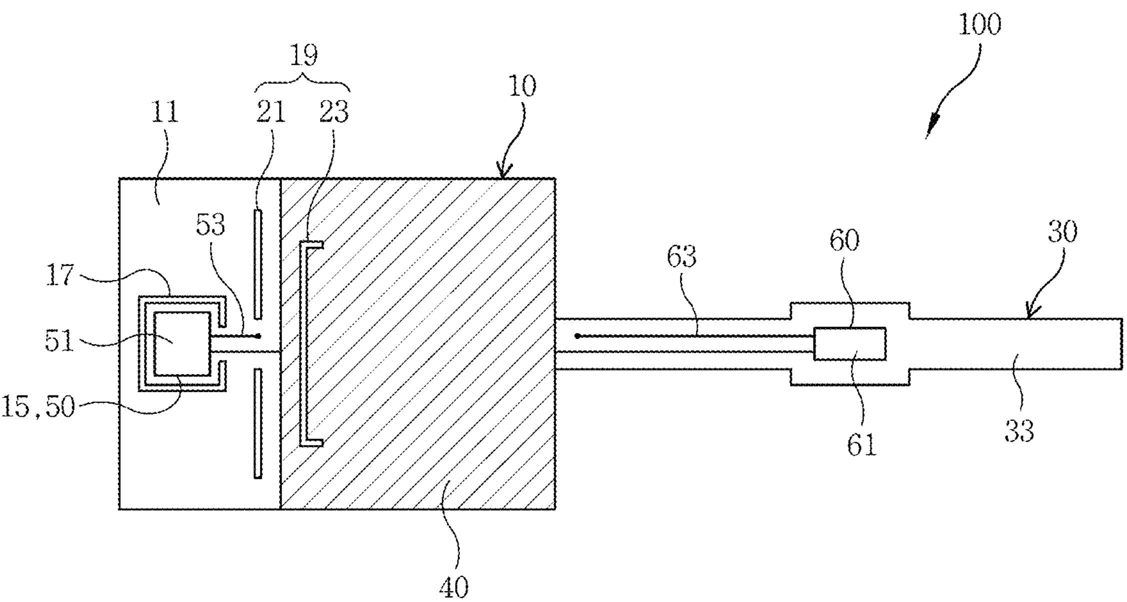
FIG. 4 is a plan view illustrating a lower surface of the wearable temperature patch according to an embodiment of the present disclosure.
Figures 5, 6:
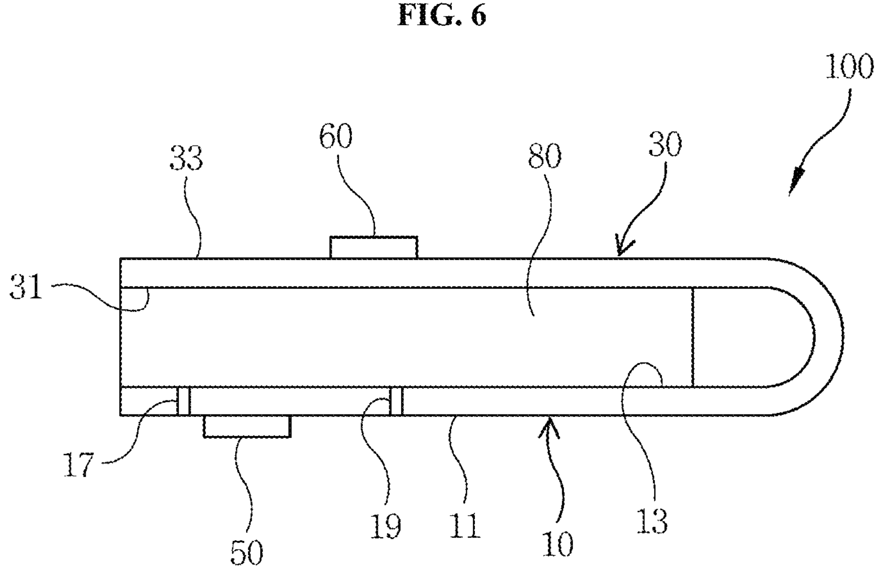
FIG. 5 is a plan view illustrating an upper surface of the wearable temperature patch according to an embodiment of the present disclosure.
FIG. 6 is a cross-sectional view illustrating the wearable temperature patch, in a state where a second base film is bent over a first base film, according to an embodiment of the present disclosure.

FIG. 4 is a plan view illustrating a lower surface of the wearable temperature patch 100 according to an embodiment of the present disclosure. FIG. 5 is a plan view illustrating an upper surface of the wearable temperature patch 100 according to an embodiment of the present disclosure. FIG. 6 is a cross-sectional view illustrating the wearable temperature patch 100, in a state where a second base film 30 is bent over a first base film 10, according to an embodiment of the present disclosure.

Referring to FIGS. 4 to 6, the wearable temperature patch 100 according to this embodiment includes the flexible base films 10 and 30 and the skin temperature sensor 50 and may further include the external temperature sensor 60, the ground layer 40, the heat-generating element 70, the inertia measurer 79, and a protective layer 80.

The base films 10 and 30 are insulating films made of a flexible plastic material. The material of the base films 10 and 30 may include, but is not limited to, polyimide, polyethersulphone (PES), poly acrylate (PAR), polyetherimide (PEI), polyethylene naphthalate (PEN), polyethylene terephthalate (PET), polyphenylene sulfide (PPS), polyallylate, polycarbonate (PC), cellulose triacetate (CTA), or cellulose acetate propinonate (CAP).

The base films 10 and 30 include the first base film 10 and the second base film 30. Each of the first and second base films 10 and 30 has an upper surface 13 or 33 and a lower surface 11 or 31 opposite to the upper surface 13 or 33. Because the second base film 30 is bent and positioned over the upper surface 13 of the first base film 10, the lower surface 11 of the first base film 10 and the upper surface 33 of the second base film 30 are coplanar and the upper surface 13 of the first base film 10 and the lower surface 31 of the second base film 30 are coplanar in the plan views of FIGS. 4 and 5.

The skin temperature sensor 50 and the ground layer 40 are formed on the lower surface 11 of the first base film 10. The skin temperature sensor 50 and the ground layer 40 are formed to be spaced apart from each other. The heat-generating element 70 is mounted on the upper surface 13 of the first base film 10.

The external temperature sensor 60 is formed on the upper surface 33 of the second base film 30. The second base film 30 is formed to be narrower than the first base film 10 so that it can be easily bent with respect to the first base film 10 and positioned over the first base film 10.

When the second base film 30 is bent with respect to the first base film 10, the lower surface 11 of the first base film 10 on which the skin temperature sensor 50 is mounted faces the skin, and the external temperature sensor 60 faces the outside. That is, after the lower surface 11 of the first base film 10 and the upper surface 33 of the second base film 30 are positioned to face downward, the second base film 30 is bent so that its lower surface 31 is positioned over the upper surface 13 of the first base film 10.

The ground layer 40 is formed on the lower surface 11 of the first base film 10, but this is not a limitation. For example, the ground layer 40 may be formed inside the first base film 10.

The skin temperature sensor 50 is a temperature sensor of resistance film type based on a platinum material, and includes an internal sensor 51 and an internal electrode 53. The internal sensor 51 measures the body temperature (skin temperature) of a contacted skin. The internal electrode 53 is connected to the internal sensor 51 and transmits the measured skin temperature to the storage 73 or the controller 75. The internal electrode 53 may be formed of a plurality of lines, one of the plurality of lines may be connected to the ground layer 40, and the other may be connected to the storage 73 or the controller 75 to which the measured skin temperature is transmitted.

The guard slot 17 is formed to penetrate the first base film 10 around the skin temperature sensor 50. The guard slot 17 is formed to surround the skin temperature sensor 50 and is not formed in a portion where the internal electrode 53 is formed. That is, the guard slot 17 is formed to surround the internal sensor 51 except for a portion where the internal electrode 53 connected to the internal sensor 51 is drawn out.

The boundary slot 19 includes the first boundary slot 21 and the second boundary slot 23. The first boundary slot 21 may be formed near both sides of the internal electrode 53. The second boundary slot 23 may be formed in the ground layer 40 in a form that covers the controller 75 in a direction of the skin temperature sensor 50. The second boundary slot 23 is formed to penetrate the ground layer 40 and the first base film 10.

As described above, by forming the guard slot 17 and/or the boundary slot 19 around the skin temperature sensor 50, the wearable temperature patch 100 according to this embodiment can block heat conduction to the skin temperature sensor 50 through the base films 10 and 30. That is, it is possible to reduce the influence of internal heat-affecting factors by the guard slot 17 and/or the boundary slot 19 at the skin temperature measured by the skin temperature sensor 50.

The heat-generating element 70 is mounted on the upper surface 13 of the first base film 10. The heat-generating element 70 is mounted on the upper surface 13 of the first base film 10 opposite to the lower surface 11 of the first base film 10 on which the ground layer 40 is formed.

The protective layer 80 protects the heat-generating element 70 from the external environment. The protective layer 80 may be formed by laminating a protective film of a plastic resin on the upper surface 13 of the first base film 10 where the heat-generating element 70 is mounted. Alternatively, the protective layer 80 may be formed by coating or molding a liquid plastic resin. As a material of the protective layer 80, a plastic material or a nonwoven fabric capable of providing flexibility to the first base film 10 may be used.

The second base film 30 bent over the first base film 10 may be attached on the protective layer 80.

The external temperature sensor 60 is mounted on the upper surface 33 of the second base substrate. The external temperature sensor 60 is a temperature sensor of resistance film type based on a platinum material, and includes an external sensor 61 and an external electrode 63. The external sensor 61 measures the external temperature applied to the wearable temperature patch 100 from the opposite side to the skin. The external electrode 63 is connected to the external sensor 61 and transmits the measured external temperature to the storage 73 or the controller 75. The external electrode 63 may be formed of a plurality of lines, one of the plurality of lines may be connected to the ground layer 40, and the other may be connected to the storage 73 or the controller 75 to which the measured external temperature is transmitted.

As such, the external temperature sensor 60 measures the external temperature according to the external heat-affecting factor.

Figure 7:
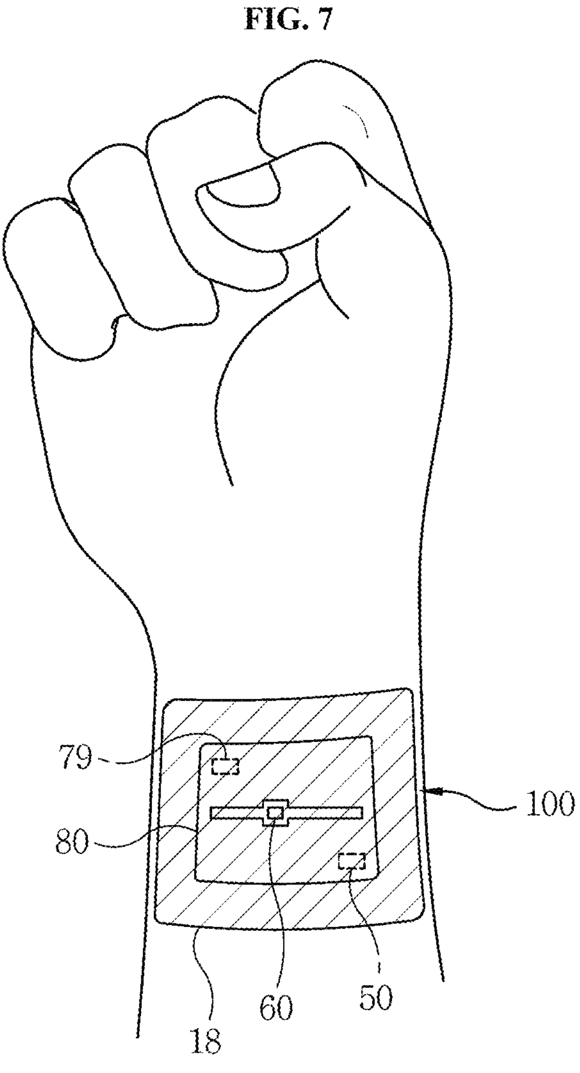
FIG. 7 is a diagram illustrating the wearable temperature patch attached to the wrist according to an embodiment of the present disclosure.

FIG. 7 is a diagram illustrating the wearable temperature patch 100 attached to the wrist according to an embodiment of the present disclosure.

Referring to FIG. 7, the wearable temperature patch 100 according to this embodiment may be attached to various body parts of a target person using an attachment pad 18. FIG. 7 shows an example in which the wearable temperature patch 100 is attached to the wrist by the attachment pad 18. The attachment pad 18 may be an adhesive tape made of flexible plastic, paper, or non-woven fabric.

The wearable temperature patch 100 is attached to the wrist so that the skin temperature sensor 50 faces the skin of the wrist. The wearable temperature patch 100 is attached to the wrist so that the external temperature sensor 60 is positioned just below the attachment pad 18 and faces the outside of the wrist.

[Body Temperature Estimation Method]

Now, the body temperature estimation method using the body temperature estimation system according to this embodiment will be described with reference to FIGS. 2 and 8 to 16.

Body Temperature Estimation Method According to First Example

Figure 8:
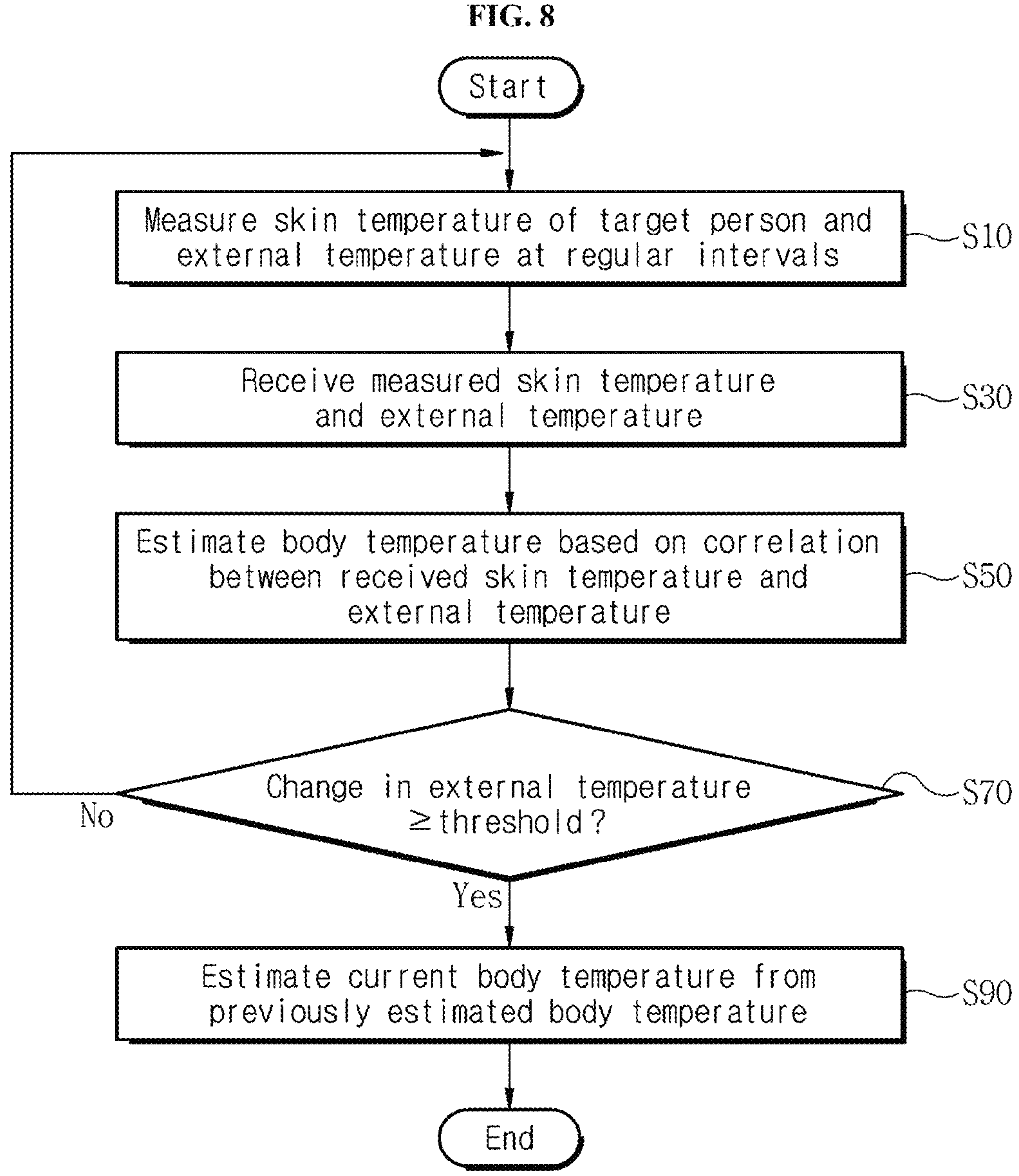
FIG. 8 is a flowchart illustrating a first example of a body temperature estimation method in consideration of changes in the external temperature, performed by a body temperature estimation system, according to an embodiment of the present disclosure.

FIG. 8 is a flowchart illustrating a first example of a body temperature estimation method in consideration of changes in the external temperature, performed by a body temperature estimation system, according to an embodiment of the present disclosure.

First, at step S10, the wearable temperature patch 100 attached to the skin of the target person continuously measures the skin temperature and the external temperature at regular intervals. The regular interval may be several seconds, for example, 5 seconds. The wearable temperature patch 100 time-synchronizes the measured skin temperature and external temperature and outputs them to the management terminal 200.

Next, at step S30, the management terminal 200 receives the skin temperature and the external temperature.

Next, at step S50, the management terminal 200 estimates the body temperature, based on a correlation between the received skin temperature and the received external temperature. That is, based on the time the skin temperature is measured, the management terminal 200 extracts the external temperature that affects the skin temperature according to the heat transfer characteristics of the wearable temperature patch 100. The management terminal 200 estimates the body temperature of the target person at the time the skin temperature is measured, from the correlation between the skin temperature and the extracted external temperature. For example, the body temperature can be estimated by Equation 1.

Next, at step S70, the management terminal 200 monitors the amount of change in the external temperature per monitoring time. That is, the management terminal 200 determines whether the amount of change in the external temperature is greater than or equal to a threshold. Here, the monitoring time and the threshold are reference values for determining a sudden change in the external temperature. The monitoring time may be determined between 1 minute and 5 minutes. The threshold may be determined at 0.5 or higher.

If the determination result at the step S70 is less than the threshold, the process is performed again from the step S10.

If the determination result at the step S70 is greater than or equal to the threshold, at step S90 the management terminal 200 estimates the current body temperature from the body temperature estimated before the external temperature change greater than or equal to the threshold occurs.

The above-described body temperature estimation method according to the first example was confirmed through specific experimental examples shown in FIGS. 9 to 14. The wearable temperature patch 100 according to this embodiment was attached to the wrist of the target person as shown in FIG. 7. The wearable temperature patch 100 measured skin temperature, external temperature, and movement information generated in the process of a target person naturally moving through various spaces during daily life.

Figure 9:
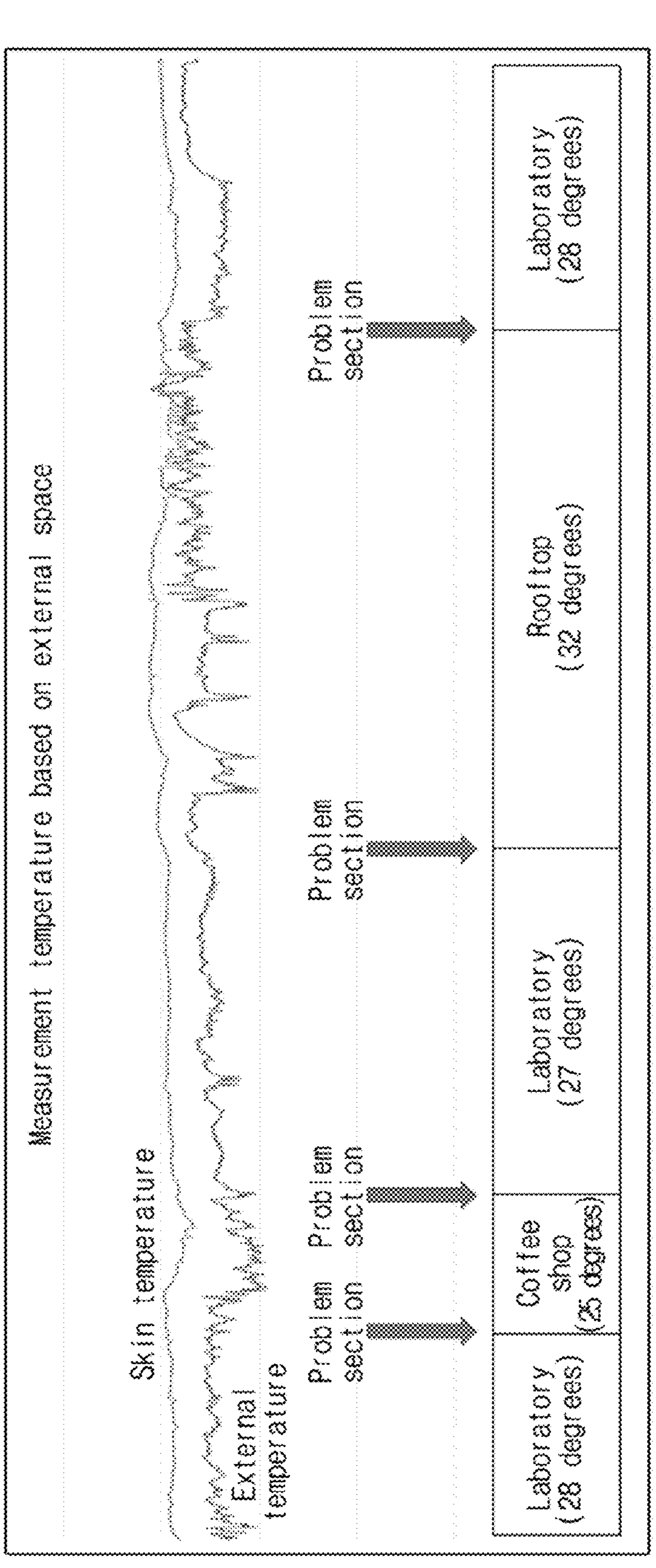
FIG. 9 is a graph showing the skin temperature and the external temperature synchronized with spatial movements of a target person.

FIG. 9 is a graph showing the skin temperature and the external temperature synchronized with spatial movements of a target person.

Referring to FIG. 9, while the target person with the wearable temperature patch is moving from time to time to the laboratory, coffee shop, and rooftop, the skin temperature and external temperature measured every 5 seconds are synchronized with the location and temperature of the space. In this case, problem sections may occur as indicated by red arrows. The problem section refers to a section that becomes a boundary in space and time when the target person moves from a first space to a second space. It can be seen that a sudden change in the external temperature occurs in the problem section. In this case, the laboratory has a space temperature of 27-28 degrees, the coffee shop has a space temperature of 25 degrees, and the rooftop has a space temperature of 32 degrees.

Such a problem section may be caused not only by movement between spaces having different temperatures, but also by changes in space temperature within the same space as shown in FIG. 10.

FIG. 10 is a graph showing the skin temperature and the external temperature measured by the wearable temperature patch in an environment of a rapid change in the spatial temperature.

Referring to FIG. 10, in a state where the target person was located indoors in the laboratory, the skin temperature and the external temperature before and after operating the air conditioner were measured using the wearable temperature patch at 5-second intervals. The space temperature before the operation of the air conditioner was measured to be 28 degrees, and the space temperature after the operation of the air conditioner was measured to be 26 degrees. Synchronizing the measured space temperature, skin temperature, and external temperature with time, it is as shown in FIG. 10.

As such, when a sudden change in the space temperature occurs, it can be seen that the external temperature measured at the wrist rapidly drops within 5 minutes and then is constantly measured by a partial increase in the external temperature within 10 minutes.

It can be seen that the measured skin temperature shows a similar pattern to the change in the measured external temperature although the amount of change is not large compared to the external temperature.

Figure 11:
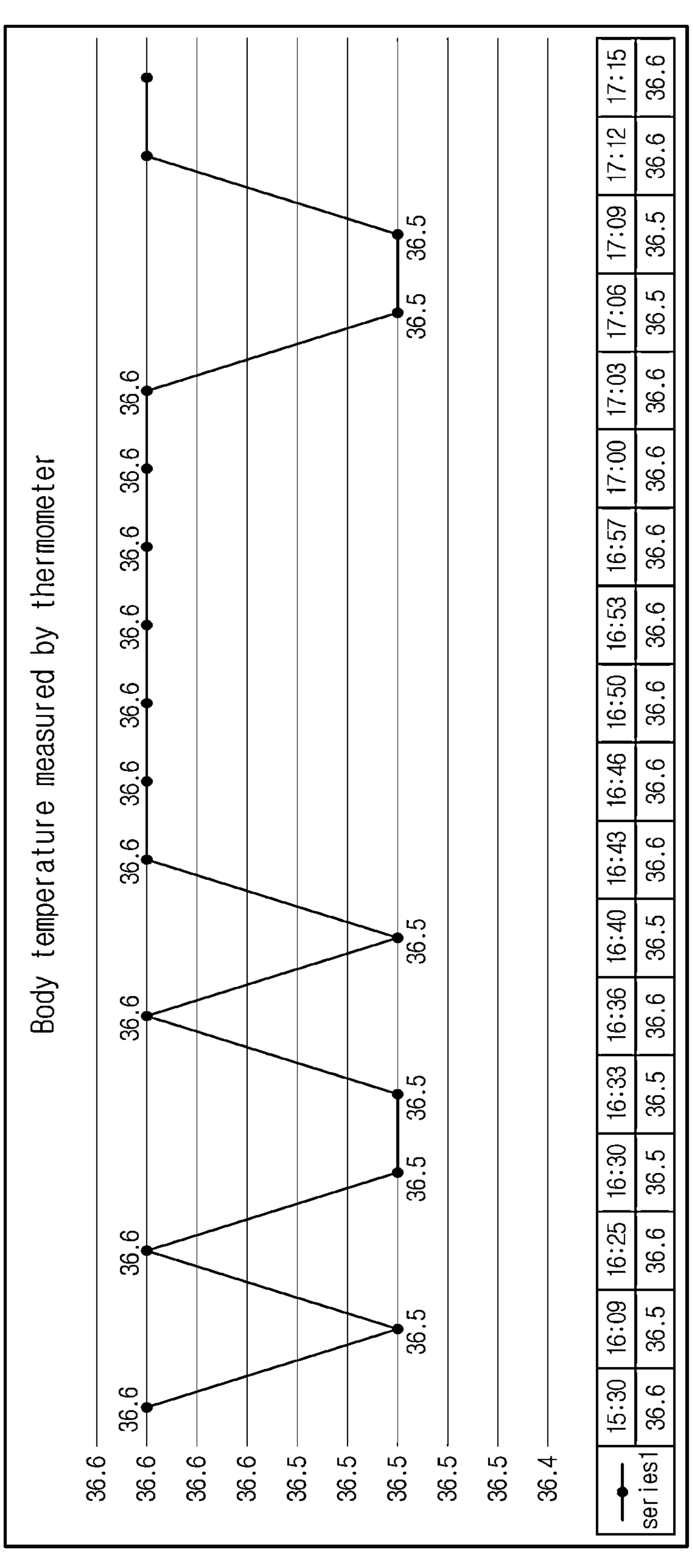
FIG. 11 is a graph showing the body temperature measured with a body part thermometer in the environment of rapid space temperature change of FIG. 10.

FIG. 11 is a graph showing the body temperature measured with a body part thermometer in the environment of rapid space temperature change of FIG. 10.

Referring to FIG. 11, the body temperature was measured using a commercial thermometer (IRT6510/Brown) that obtained approval from the Ministry of Food and Drug Safety as a body part thermometer.

As a result of the measurement, it can be seen that the body temperature is constantly maintained at 36.5 to 36.6 degrees even in an environment of rapid temperature change. Moreover, considering that the allowable error range of the commercial thermometer is ±0.3 degrees, it can be seen that the body temperature measured with the commercial thermometer is kept very constant.

Figure 12:
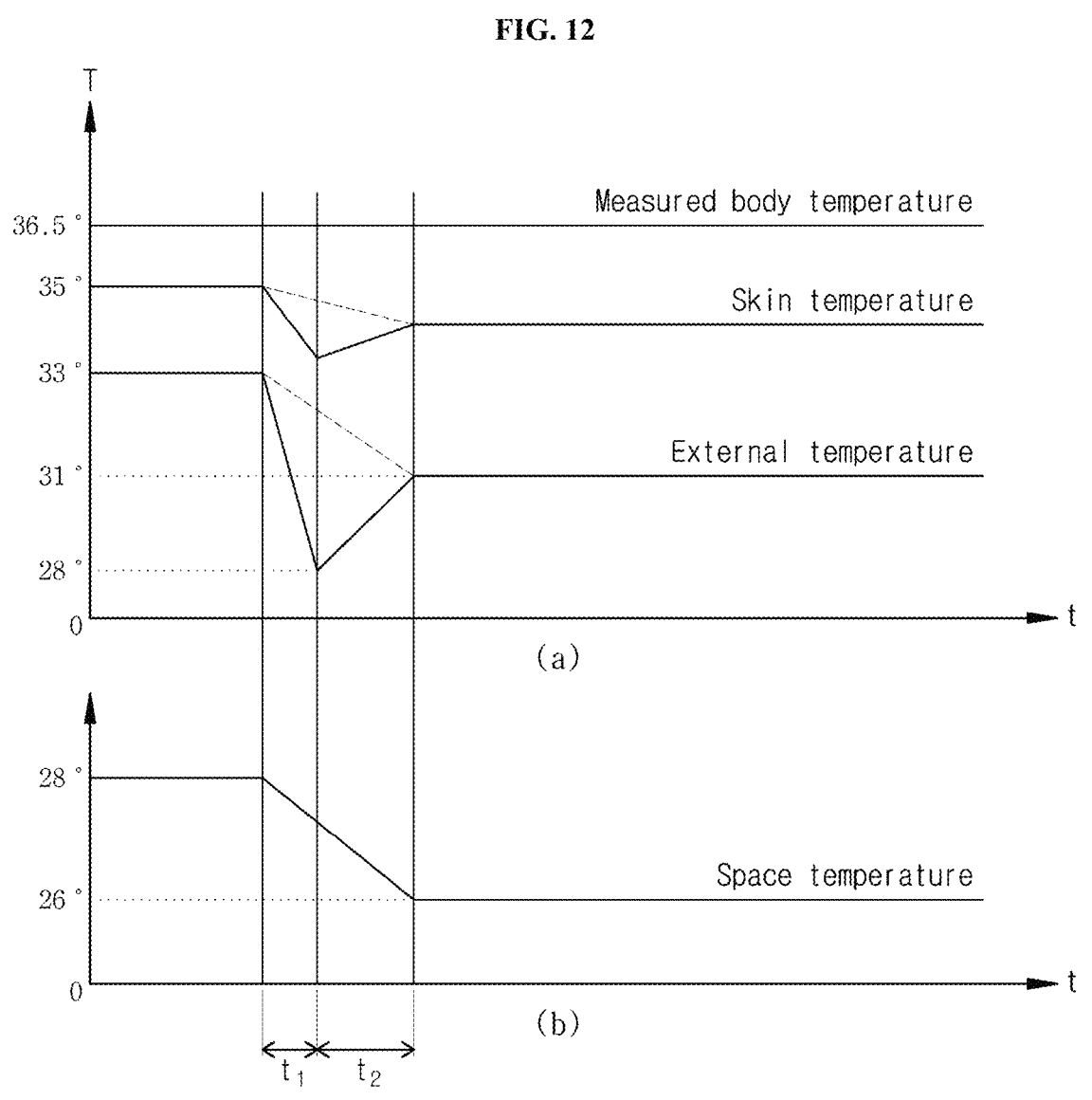
Figure 13:
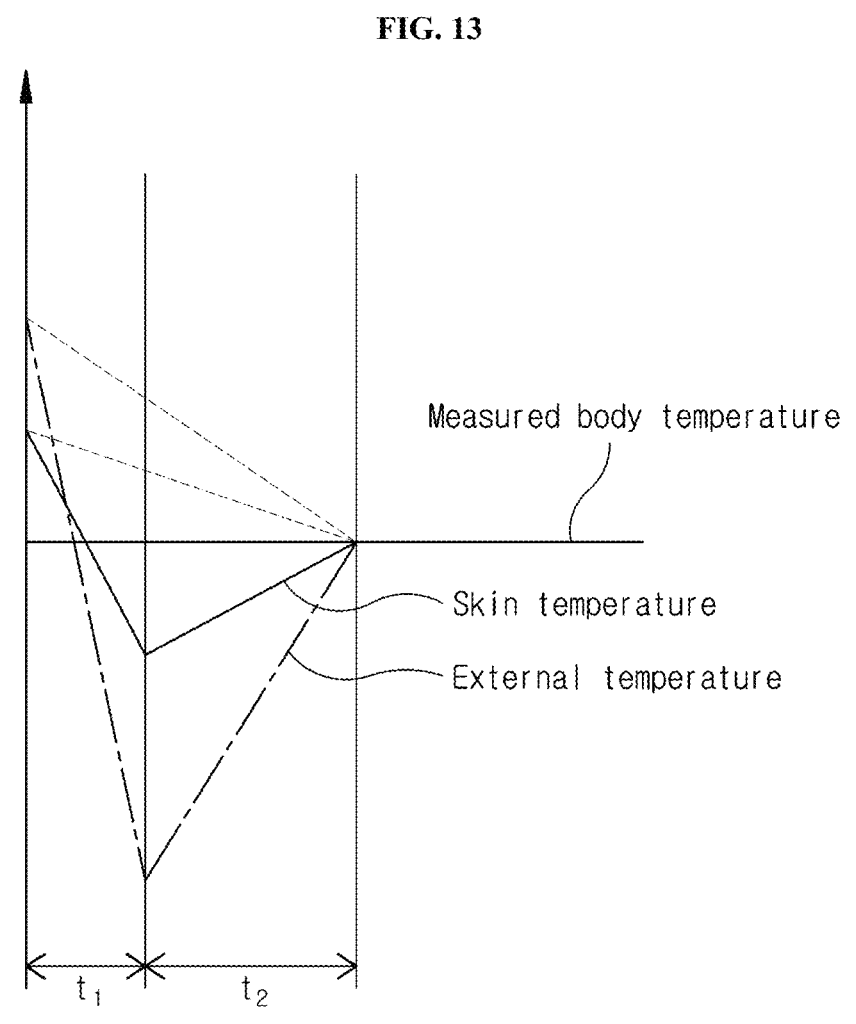

The measurement results of FIGS. 10 and 11 are schematically expressed as shown in FIGS. 12 and 13. FIG. 12 is a graph showing the skin temperature, external temperature, and body temperature measured in the environment of rapid space temperature change of FIG. 10. FIG. 13 is a graph showing normalization of the skin temperature, external temperature, and body temperature measured in a problem section of FIG. 12.

Referring to FIGS. 12 and 13, it can be seen that the body temperature is maintained constant even though the measured skin temperature and external temperature are changed according to the change of the space temperature.

The body temperature estimated using the correlation between the external temperature and skin temperature measured by the wearable temperature patch in a general environment where a sudden change in the space temperature does not occur, that is, in a space where a constant temperature is maintained, can be reliable.

On the other hand, when a sudden change in the space temperature occurs, it can be seen that the external temperature measured at the wrist rapidly drops within 5 minutes ($t_1$) and then is constantly measured by a partial increase in the external temperature within 10 minutes ($t_2$).

Therefore, when the temperature of an indoor space changes rapidly due to the movement from the outdoor to the indoor or the operation of an air conditioner or heater, the body temperature estimated using the correlation between the external temperature and skin temperature measured in the problem section where the sudden temperature change occurs has a large error from the actually measured body temperature.

As shown in FIG. 13, if the skin temperature, external temperature, and measured body temperature in the problem section are normalized and compared, it can be seen that after about 15 minutes ($t_1+t_2$) from the occurrence of the temperature change, the skin temperature, external temperature, and measured body temperature are converging to a constant temperature by adapting to the space temperature change.

It can be seen that the measured skin temperature does not change much compared to the external temperature, but changes in a pattern similar to the measured external temperature change.

Based on changes in skin temperature, external temperature, and body temperature measured in such a sudden temperature change environment, this embodiment provides a method for estimating the body temperature as follows.

FIG. 14 is a table showing the skin temperature, the external temperature, and the amount of change in temperature measured in units of one minute in the environment of rapid space temperature change of FIG. 10.

Referring to FIG. 14, the table shows the skin temperature and external temperature measured in units of one minute in the environment of rapid space temperature change. Measured data are the skin temperature and external temperature measured by the wearable temperature patch according to this embodiment. In the table, the "Out" column denotes the external temperature, and the "In" column denotes the skin temperature.

In the table, the measured data in the first green row is the measured data before the sudden temperature change occurs.

Thereafter, a sudden change in space temperature occurred, and data measured in units of one minute were recorded in the second to fifth green rows. The data visualized in the Out/In column on the right side of the table indicates a difference between the previously measured data and the currently measured data. In the table, the "Out" column on the right indicates the amount of change in the external temperature in units of one minute, and the "In" column indicates the amount of change in the skin temperature in units of one minute.

For example, from the values recorded in the "Out" column with pink, it can be seen that the temperature changes of 0.67 in the second, 1.34 in the third, 1.07 in the fourth, and 1.82 in the fifth occur, respectively.

Such temperature changes are phenomena that exceed a temperature change that may occur due to an effect of a change in the body temperature. That is, because such changes in the external temperature are considered as influence caused by changes in the space temperature, it is necessary to filter these influence values to accurately measure a change in the body temperature caused by a change in the body.

The present embodiment provides a method for estimating body temperature when a threshold for judging a sudden change in external temperature is 0.5. That is, the body temperature estimation method according to this embodiment performs the body temperature estimation by using, as a reference value, the measurement data before the sudden temperature change occurs for the first time.

According to the table, the first measurement data, 34.05 (Out)/35.6(In), is used as a reference value, and the body temperature is estimated using a correlation between the skin temperature and the external temperature in a section of rapid temperature change. That is, the body temperature estimated by the first measurement data is estimated as the current body temperature in the rapid temperature change section.

When the first change in the external temperature is detected as a sudden change of 0.67 degrees (in the case of 0.5 degrees or more), the external temperature is corrected to 34.05 degrees even though the change in the external temperature is 0.67 degrees. Also, the skin temperature is corrected to 35.6 degrees even though the change in the skin temperature is −0.1 degrees. That is, the current external temperature and skin temperature are corrected using, as reference values, the external temperature and skin temperature measured before the sudden temperature change occurs.

Even when the second change in the external temperature is detected as a sudden change of 1.34 degrees, the external temperature is corrected to 34.05 degrees even though the change in the external temperature is 1.34 degrees. Also, the skin temperature is corrected to 35.6 degrees even though the change in the skin temperature is 0.09 degrees.

In addition, even when the third, fourth, and fifth rapid temperature changes are detected, the external temperature is corrected to 34.05 degrees and the skin temperature is corrected to 35.6 degrees.

As such, when a sudden temperature change is detected, the body temperature estimation is performed by maintaining, as reference values, the external temperature and skin temperature before the sudden temperature change occurs. If a sudden temperature change is not detected, a difference between the temperature before the sudden change and the temperature stabilized after the sudden change is corrected in the same way, and the current body temperature is estimated based on the previously used correlation between the skin temperature and the external temperature.

On the other hand, when the space temperature changes rapidly, it can be seen that the external temperature changes rapidly, but the change in the skin temperature is relatively small. Therefore, when the temperature is corrected in an environment of rapid temperature change, only the external temperature is corrected as a reference value, and the current body temperature may be estimated using the correlation between the external temperature according to the reference value and the measured skin temperature. This body temperature estimation may be applied to the case where a difference between the measured skin temperature and the reference value is not large as the space temperature changes. For example, this difference value may be 0.2 or less.

Body Temperature Estimation Method According to Second Example

Figure 15:
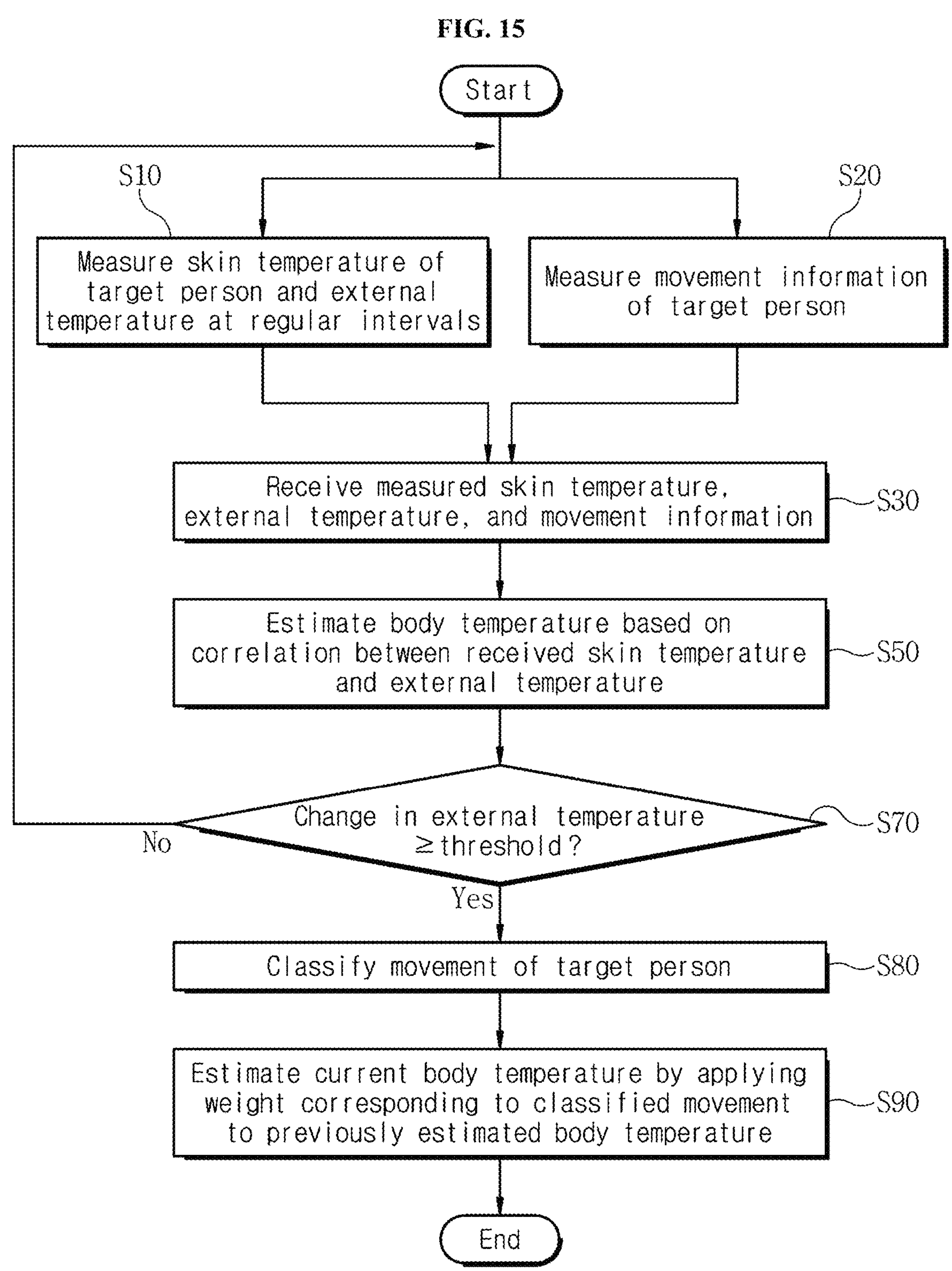
FIG. 15 is a flowchart illustrating a second example of a body temperature estimation method in consideration of changes in the external temperature, performed by a body temperature estimation system, according to an embodiment of the present disclosure.

Although the method for estimating body temperature according to the first example is to estimate the body temperature by reflecting a sudden temperature change in an external environment, the present disclosure is not limited thereto. For example, as shown in FIG. 15, the body temperature may be estimated by reflecting both the rapid temperature change of the external environment and the movement of the target person.

Now, the second example of the method for estimating body temperature will be described with reference to FIGS. 2 and 15. FIG. 15 is a flowchart illustrating a second example of a body temperature estimation method in consideration of changes in the external temperature, performed by a body temperature estimation system, according to an embodiment of the present disclosure.

The body temperature estimation method according to the second example is to estimate the body temperature by reflecting both the movement of the target person and a sudden change in the external temperature.

First, at step S10, the wearable temperature patch 100 attached to the skin of the target person measures the skin temperature and the external temperature at regular intervals. The regular interval may be several seconds, for example, 5 seconds. The wearable temperature patch 100 time-synchronizes the measured skin temperature and external temperature and outputs them to the management terminal 200.

At step S20, the wearable temperature patch 100 measures the movement of the target person. The wearable temperature patch 100 time-synchronizes the measured movement information with the measured skin temperature and external temperature and outputs them to the management terminal 200.

Although an example in which the steps S10 and S20 are performed in parallel is shown, the step S20 may be performed after or before the step S10.

Next, at step S30, the management terminal 200 receives the skin temperature, the external temperature, and the movement information.

Next, at step S50, the management terminal 200 estimates the body temperature, based on a correlation between the received skin temperature and the received external temperature. That is, based on the time the skin temperature is measured, the management terminal 200 extracts the external temperature that affects the skin temperature according to the heat transfer characteristics of the wearable temperature patch 100. The management terminal 200 estimates the body temperature of the target person at the time the skin temperature is measured, from the correlation between the skin temperature and the extracted external temperature. For example, the body temperature can be estimated by Equation 1.

Next, at step S70, the management terminal 200 monitors the amount of change in the external temperature per monitoring time. That is, the management terminal 200 determines whether the amount of change in the external temperature is greater than or equal to a threshold. Here, the monitoring time and the threshold are reference values for determining a sudden change in the external temperature. The monitoring time may be determined between 1 minute and 5 minutes. The threshold may be determined at 0.5 or higher.

If the determination result at the step S70 is less than the threshold, the process is performed again from the step S10.

If the determination result at the step S70 is greater than or equal to the threshold, at step S80 the management terminal 200 classifies the movement of the target person based on the received movement information. That is, for the sudden temperature change determined at the step S70, the management terminal 200 utilizes the received movement information and thereby distinctively determines whether the temperature change is due to the spatial movement of the target person or due to the operation of the air conditioner or heater without movement of the target person.

Then, at step S90, the management terminal 200 estimates the current body temperature by using the body temperature estimated before the external temperature change greater than or equal to the threshold occurs, and by also reflecting a weight corresponding to the classified movement information to the previously estimated body temperature.

Figure 16:
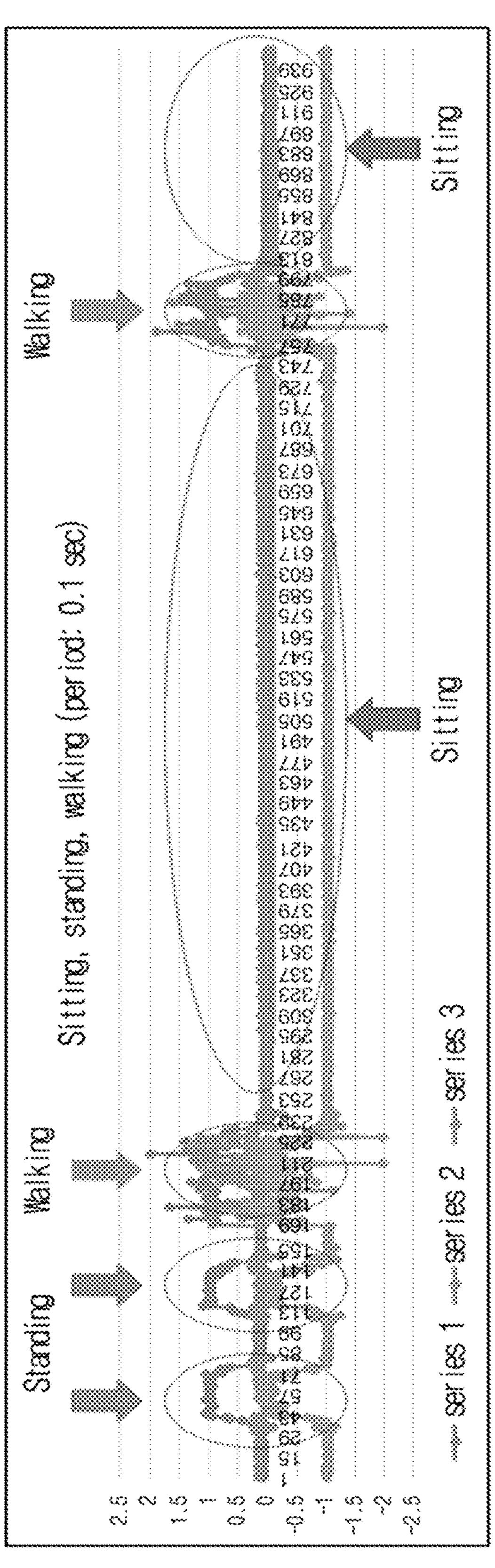
FIG. 16 is a graph showing measurement data of an inertia measurer according to movements of a target person.

FIG. 16 is a graph showing measurement data of an inertia measurer according to movements of a target person.

The movement information according to the movements of the target person to which the wearable temperature patch 100 is attached is measured by the inertia measurer 79. In this embodiment, the movement information was measured every 0.1 second by using an acceleration sensor as the inertia measurer 79, and the measured movement information can be visually shown as in FIG. 16.

Referring to FIG. 16, it can be seen that the higher the movement, the higher the peak appears. It can be seen that the peak of movement appears higher in the order of sitting, standing, and walking.

As described above, according to the body temperature estimation method of the second example, it is possible to more accurately estimate the body temperature of the target person by reflecting the movement information in an environment in which a sudden change in the external temperature occurs.

While the present disclosure has been particularly shown and described with reference to an exemplary embodiment thereof, it will be understood by those skilled in the art that various changes in form and details may be made therein without departing from the scope of the present disclosure as defined by the appended claims.

This work was supported by the Energy Demand Management Core Technology Development of the Korea Institute of Energy Technology Evaluation and Planning (KETEP) granted financial resource from the Ministry of Trade, Industry & Energy, Republic of Korea (No. 20212020900380).

What is claimed is:

1. A wearable temperature patch attached to a target person's skin and continuously estimating a body temperature, comprising:
- a flexible base film including a first base film and a second base film connected to the first base film and bent over the first base film;
- a skin temperature sensor mounted on a lower surface of the first base film, being in contact with the target person's skin, and configured to measure a skin temperature at regular intervals;
- an external temperature sensor mounted on an upper surface of the second base film and configured to measure an external temperature outside the target person's skin at the regular intervals;
- an inertia measurer installed on the first base film and configured to measure movements of the target person;
- a controller installed on the first base film, and configured to:
  - receive measured movement information from the inertia measurer,
  - receive the measured skin temperature from the skin temperature sensor,
  - receive the measured external temperature from the external temperature sensor,
  - estimate the body temperature based on a correlation between the skin temperature and the external temperature,
  - monitor a change in the external temperature per monitoring time, and determine whether the change in the external temperature is greater than or equal to a threshold,
  - estimate a current body temperature based on the body temperature estimated before the change in the external temperature greater than or equal to the threshold occurs, in response to the change in the external temperature being greater than or equal to the threshold, and
  - correct the estimated current body temperature based on the received movement information; and
- a ground layer formed on the first base film to be spaced apart from a mounting region in which the skin temperature sensor is mounted,
- wherein the first base film has a heat conduction blocking slot formed for blocking heat conduction to the mounting region, and
- wherein the heat conduction blocking slot includes a guard slot formed in the first base film along circumference of the skin temperature sensor, and a boundary slot formed at a boundary between the mounting region and a region in which the ground layer is formed,
- wherein the controller is configured to calculate the amount of change in the external temperature by Equation 1 below, in response to the change amount of the external temperature calculated in the monitoring time of $(t_{i+1}-t_i)$ being greater than or equal to the threshold, replace the external temperature and skin temperature measured at time $t_{i+1}$ with the external temperature and skin temperature measured at time $t_i$, and estimate the body temperature at time $t_{i+1}$ based on the correlation between the replacement skin temperature and external temperature, $$\Delta T = T_i - T_{i+1} \quad \text{[Equation 1]}$$

$T_i$: External temperature at time $t_i$ $T_{i+1}$: External temperature at time $t_{i+1}$ $t_{i+1}-t_i$: Monitoring time.

2. The wearable temperature patch of claim 1, wherein the controller is configured to classify the received movement information according to a movement type and a movement intensity, and estimate the current body temperature by adding a weight corresponding to the classified movement information.

3. The wearable temperature patch of claim 1, wherein the monitoring time is 1 minutes to 5 minutes.

4. The wearable temperature patch of claim 3, wherein the threshold is 0.5 degrees/the monitoring time or higher.

5. The wearable temperature patch of claim 1, wherein the correlation is expressed by Equation 2 below, $$T_{est}(t)=(k*T_2(t-\alpha)-T_3(t))/(k-1) \quad \text{[Equation 2]}$$

$T_{est}$: Estimated body temperature k: External influence proportional constant $T_2$: External temperature $T_3$: Skin temperature t: Measurement time (unit: minutes)

$\alpha$: Temperature transfer time (unit: minutes).

6. A body temperature estimation system continuously estimating a body temperature of a target person, comprising:
- a temperature measurement unit attached to a skin of the target person and configured to measure a skin temperature and an external temperature;
- a movement measurement unit configured to measure movements of the target person; and
- a body temperature estimation unit configured to:
  - receive measured movement information from the movement measurement unit,
  - receive the skin temperature and the external temperature from the temperature measurement unit,
  - estimate the body temperature based on a correlation between the skin temperature and the external temperature,
  - monitor a change in the external temperature per monitoring time, and determine whether the change in the external temperature is greater than or equal to a threshold,
  - estimate a current body temperature based on the body temperature estimated before the change in the external temperature greater than or equal to the threshold occurs, in response to the change in the external temperature being greater than or equal to the threshold, and
  - correct the estimated current body temperature based on the received movement information,
- wherein the temperature measurement unit includes:
  - a flexible base film including a first base film and a second base film connected to the first base film and bent over the first base film;
  - a skin temperature sensor mounted on a lower surface of the first base film, being in contact with the skin, and configured to measure the skin temperature;
  - an external temperature sensor mounted on an upper surface of the second base film and configured to measure the external temperature; and
  - a ground layer formed on the first base film to be spaced apart from a mounting region in which the skin temperature sensor is mounted,
- wherein the first base film has a heat conduction blocking slot formed for blocking heat conduction to the mounting region, and wherein the heat conduction blocking slot includes a guard slot formed in the first base film along circumference of the skin temperature sensor, and a boundary slot formed at a boundary between the mounting region and a region in which the ground layer is formed, wherein the body temperature estimation unit is configured to:

calculate the amount of change in the external temperature by Equation 1 below, in response to the change amount of the external temperature calculated in the monitoring time of ($t_{i+1}-t_i$) being greater than or equal to the threshold, replace the external temperature and skin temperature measured at time $t_{i+1}$ with the external temperature and skin temperature measured at time $t_i$, and estimate the body temperature at time $t_{i+1}$ based on the correlation between the replacement skin temperature and external temperature, $$\Delta T=T_i-T_{i+1} \quad \text{[Equation 1]}$$

$T_i$: External temperature at time $t_i$ $T_{i+1}$: External temperature at time $t_{i+1}$ $t_{i+1}-t_i$: Monitoring time.

7. A body temperature estimation system continuously estimating a body temperature of a target person, comprising:

a wearable temperature patch attached to a skin of the target person and configured to continuously estimate the body temperature; and a management terminal configured to receive the estimated body temperature of the target person from the wearable temperature patch, wherein the wearable temperature patch includes:

a flexible base film including a first base film and a second base film connected to the first base film and bent over the first base film;

a skin temperature sensor mounted on a lower surface of the first base film, being in contact with the target person's skin, and configured to measure a skin temperature;

an external temperature sensor mounted on an upper surface of the second base film and configured to measure an external temperature outside the target person's skin;

an inertia measurer installed on the first base film and configured to measure movements of the target person;

a controller installed on the first base film and configured to:

receive measured movement information from the inertia measurer, receive the measured skin temperature from the skin temperature sensor, receive the measured external temperature from the external temperature sensor, estimate the body temperature based on a correlation between the skin temperature and the external temperature, monitor a change in the external temperature per monitoring time, and determine whether the change in the external temperature is greater than or equal to a threshold, estimate a current body temperature based on the body temperature estimated before the change in the external temperature greater than or equal to the threshold occurs, in response to the change in the external temperature being greater than or equal to the threshold, and correct the estimated current body temperature based on the received movement information; and a ground layer formed on the first base film to be spaced apart from a mounting region in which the skin temperature sensor is mounted, wherein the first base film has a heat conduction blocking slot formed for blocking heat conduction to the mounting region, and wherein the heat conduction blocking slot includes a guard slot formed in the first base film along circumference of the skin temperature sensor, and a boundary slot formed at a boundary between the mounting region and a region in which the ground layer is formed, wherein the controller is configured to:

calculate the amount of change in the external temperature by Equation 1 below, in response to the change amount of the external temperature calculated in the monitoring time of ($t_{i+1}-t_i$) being greater than or equal to the threshold, replace the external temperature and skin temperature measured at time $t_{i+1}$ with the external temperature and skin temperature measured at time $t_i$, and estimate the body temperature at time $t_{i+1}$ based on the correlation between the replacement skin temperature and external temperature, $$\Delta T=T_i-T_{i+1} \quad \text{[Equation 1]}$$

$T_i$: External temperature at time $t_i$ $T_{i+1}$: External temperature at time $t_{i+1}$ $t_{i+1}-t_i$: Monitoring time.

* * * * *